(12) United States Patent
Saunier

(10) Patent No.: US 7,578,856 B2
(45) Date of Patent: Aug. 25, 2009

(54) DYEING COMPOSITIONS COMPRISING AT LEAST ONE AMINOPYRAZOLOPYRIDINE OXIDATION BASE, AT LEAST ONE COUPLER AND AT LEAST ONE $C_4$-$C_{30}$ POLYOL AND METHODS AND USE THEREOF

(75) Inventor: Jean-Baptiste Saunier, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/149,872

(22) Filed: May 9, 2008

(65) Prior Publication Data

US 2008/0289122 A1 Nov. 27, 2008

Related U.S. Application Data

(60) Provisional application No. 60/924,852, filed on Jun. 1, 2007.

(51) Int. Cl.
*A61Q 5/10* (2006.01)
*C07D 515/02* (2006.01)

(52) U.S. Cl. ............... 8/405; 8/406; 8/407; 8/410; 8/411; 8/435; 8/568; 8/570; 8/571; 8/574; 8/606; 8/669; 8/670; 546/121

(58) Field of Classification Search ............... 8/405, 8/406, 407, 410, 435, 568, 570, 571, 606, 8/669, 670; 546/121
See application file for complete search history.

(56) References Cited

U.S. PATENT DOCUMENTS

| | | | |
|---|---|---|---|
| 2,841,584 A | 7/1958 | Hunter | |
| 4,003,699 A | 1/1977 | Rose et al. | |
| 4,128,425 A | 12/1978 | Greenwald | |
| RE30,199 E | 1/1980 | Rose et al. | |
| 4,823,985 A | 4/1989 | Grollier et al. | |
| 5,061,289 A | 10/1991 | Clausen et al. | |
| 5,234,818 A | 8/1993 | Zimmermann et al. | |
| 5,380,340 A | 1/1995 | Neunhoeffer et al. | |
| 5,457,200 A | 10/1995 | Zimmermann et al. | |
| 5,534,267 A | 7/1996 | Neunhoeffer et al. | |
| 5,663,366 A | 9/1997 | Neunhoeffer et al. | |
| 5,766,576 A | 6/1998 | Löwe et al. | |
| 6,027,538 A | 2/2000 | Vandenbossche et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 * | 5/2004 | Birault et al. | 546/121 |
| 7,091,215 B2 | 8/2006 | Hibi et al. | |
| 7,285,666 B2 | 10/2007 | Hibi et al. | |
| 2002/0032934 A1 | 3/2002 | Kravtchenko et al. | |
| 2006/0277691 A1 | 12/2006 | Saunier | |
| 2006/0277693 A1 | 12/2006 | Saunier | |
| 2007/0136959 A1 | 6/2007 | Fadli | |
| 2007/0143935 A1 | 6/2007 | Fadli et al. | |

FOREIGN PATENT DOCUMENTS

| | | |
|---|---|---|
| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| EP | 0 433 854 | 6/1991 |
| EP | 0 770 375 B1 | 5/1997 |
| EP | 1 155 680 | 11/2001 |
| EP | 1 233 743 | 8/2002 |
| EP | 1 389 618 | 2/2004 |
| EP | 1 586 302 | 10/2005 |
| EP | 1 733 714 A1 | 12/2006 |
| EP | 1 792 606 A1 | 6/2007 |
| EP | 1 792 903 A1 | 6/2007 |
| FR | 2 586 913 | 3/1987 |
| FR | 2 733 749 | 11/1996 |
| FR | 2 750 048 | 12/1997 |
| FR | 2 767 475 | 2/1999 |
| FR | 2 801 308 | 5/2001 |
| FR | 2 822 689 | 10/2002 |
| FR | 2 822 690 | 10/2002 |
| FR | 2 822 691 | 10/2002 |
| FR | 2 822 692 | 10/2002 |
| FR | 2 886 137 | 12/2006 |
| FR | 2 886 139 | 12/2006 |

(Continued)

OTHER PUBLICATIONS

STIC Search Report dated Sep. 9, 2008.*

(Continued)

*Primary Examiner*—Eisa B Elhilo
(74) *Attorney, Agent, or Firm*—Finnegan, Henderson, Farabow, Garrett & Dunner LLP

(57) ABSTRACT

Disclosed herein are compositions for dyeing keratinous fibers comprising, in an appropriate dyeing medium, at least one aminopyrazolopyridine oxidation base chosen from those of formula (I),

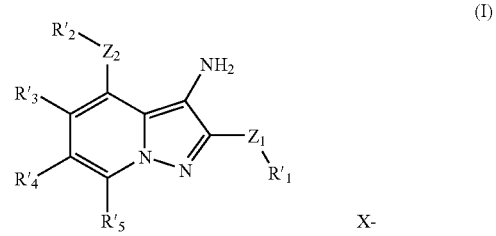

(I)

wherein it is understood that at least one of the groups $R'_1$, and $R'_2$ is chosen from cationic radicals; at least one coupler and at least one $C_4$-$C_{30}$ polyol. Dyeing methods and multi-compartment devices for use thereof.

16 Claims, No Drawings

FOREIGN PATENT DOCUMENTS

| | | |
|---|---|---|
| GB | 1 026 978 | 4/1966 |
| GB | 1 153 196 | 5/1969 |
| JP | 2-019576 | 7/1988 |
| JP | 2526099 | 7/1988 |
| JP | 5-163124 | 6/1993 |
| WO | WO 94/08969 | 4/1994 |
| WO | WO 94/08970 | 4/1994 |
| WO | WO 96/15765 | 5/1996 |
| WO | WO 01/35917 A1 | 5/2001 |
| WO | WO 02/076416 A1 | 10/2002 |
| WO | WO 02/076417 | 10/2002 |
| WO | WO 02/076418 A1 | 10/2002 |

OTHER PUBLICATIONS

English Language Derwent Abstract of non-English language document EP 0 770 375. (1997).
English Language Derwent Abstract of non-English language document JP 2-019576. (1988).
English Language Derwent Abstract of non-English language document JP 2526099. (1988).
English Language Derwent Abstract of non-English language document JP 5-163124. (1993).
English Language Derwent Abstract of non-English language document WO 02/076416 A1. (2002).
English Language Derwent Abstract of non-English language document WO 02/076418 A1. (2002).
French Search Report for FR 0754 947 (French priority application for the present application) dated Dec. 17, 2007, Examiner B. Miller.
Boros, E. et al., "A Convenient Synthesis of Pyrazolidine and 3-Amino-6, 7-dihydro1H, 5H-pyrazolo[1,2-a]pyrazol-1-one." *J. Heterocyclic Chem.*, 38: 613-616 (2001).
Cohen, S. et al., "Bicyclic, Cyclic, and Acyclic Azo Compounds, 2,3-Diazabicyclo[2,2,2]-2-octene, 3,6-Dimethyl-delta-tetrahydropyridazine and Aziosopropane." *J. Am. Chem. Soc.*, 84: 586-591 (1962).
Co-pending U.S. Appl. No. 11/594,957, filed Nov. 9, 2006.
Co-pending U.S. Appl. No. 11/594,967, filed Nov. 9, 2006.
Co-pending U.S. Appl. No. 12/149,871, filed May 9, 2008.
English language Derwent Abstract of EP 1 586 302, dated Oct. 19, 2005.
English language esp@cenet Abstract of FR 2 822 689. (2002).
English language esp@cenet Abstract of FR 2 822 690. (2002).
English language esp@cenet Abstract of FR 2 822 691. (2002).
English language esp@cenet Abstract of FR 2 822 692. (2002).
English language Derwent Abstract of WO 02/076417, dated Oct. 3, 2002.
French Search Report for FR 05/53402, the French priority application for U.S. Appl. No. 11/594,957, dated Aug. 29, 2006, Examiner G. Kyriakakou.
French Search Report for FR 05/53403, the French priority application for U.S. Appl. No. 11/594,967, dated Jul. 24, 2006, Examiner E. Baston.
French Search Report for FR 07/54948, the French priority application for U.S. Appl. No. 12/149,871, dated Dec. 13, 2007, Examiner M. Pregetter.
Fujito, H. et al., "Reaction of Pyrisnium and Isoquinolinium N-imines with Ketenethioacetals," *Heterocycles* 6(4): 379-382 (1977).
Heyman, M. et al., "An Efficient Synthesis of Bicyclic Hydrazines and Azo Alkanes," *Tetrahedron Letters* 14(30): 2859-2862 (1973).
Hudlicky, M., Reductions in Organic Chemistry, Ellis Horwood Limited, Chichester, England, 1983, pp. 1-13, 22-31.
Kharasch, N. et al, " Derivatives of Sulfenic Acids V. 1-Fluorenone Sulfir Coupounds," *J. Am. Chem. Soc.* 73: 3240-3244 (1951).
Lingens, F. et al., "Uber die Umsetzung Natulich Vorkommender Pyrimidinbasen mit Hydrazin und Methylsubstituierten Hydrazinen," *Justus Liebigs Ann. Chem.* 686: 134-145 (1965).
Magnien, E. et al., "A Re-examination of Limitations of the Hofmann Reaction", J. Org. Chem. 23: 1958, pp. 2029-2032.
March, J., Advanced Organic Chemistry, 3rd Edition, Wiley-Interscience, New York, USA, 1985, pp. 1048-1051, & 1093-1120.
Notice of Allowance mailed Jan. 12, 2009, in co-pending U.S. Appl. No. 11/594,957, Examiner R. Elhilo.
Office Action mailed Feb. 5, 2009, in co-pending U.S. Appl. No. 11/594,967, Examiner E. Elhilo.
Office Action mailed Feb. 6, 2009, in co-pending U.S. Appl. No. 12/149,871, Examiner E. Elhilo.
Office Action mailed Jun. 30, 2008, in co-pending U.S. Appl. No. 11/594,957, Examiner E. Elhilo.
Office Action mailed Jun. 30, 2008, in co-pending U.S. Appl. No. 11/594,967, Examiner E. Elhilo.
Stenzl, H. et al., "Zur Kenntnis der 3-Amino-pyrazolone-(5)", *Helvetica Chimica Acta* 33(5): 1183-1194 (1950).
STIC Search Report dated Apr. 9, 2008, for co-pending U.S. Appl. No. 11/594,957, Exmainer E. Elhilo.
STIC Search Report dated Apr. 9, 2008, for co-pending U.S. Appl. No. 11/594,967, Examiner E. Elhilo.

\* cited by examiner

DYEING COMPOSITIONS COMPRISING AT LEAST ONE AMINOPYRAZOLOPYRIDINE OXIDATION BASE, AT LEAST ONE COUPLER AND AT LEAST ONE $C_4$-$C_{30}$ POLYOL AND METHODS AND USE THEREOF

CROSS-REFERENCE TO RELATED APPLICATIONS

This application claims benefit of U.S. Provisional Application No. 60/924,852, filed Jun. 1, 2007, the contents of which are incorporated herein by reference. This application also claims benefit of priority under 35 U.S.C. § 119 to French Patent Application No. FR 0754947, filed May 9, 2007, the contents of which are also incorporated herein by reference.

FIELD OF THE INVENTION

The present disclosure relates to a dyeing composition comprising at least one aminopyrazolopyridine base, at least one coupler and at least one $C_4$-$C_{30}$ polyol. Also disclosed herein is the use of this composition for dyeing keratinous fibers and a dyeing method employing this composition.

BACKGROUND OF THE INVENTION

It is known practice to dye keratinous fibers, such as human hair, with dyeing compositions comprising oxidation dye precursors, generally known as oxidation bases, such as ortho- or para-phenylenediamines, ortho- or para-aminophenols and heterocyclic compounds. These oxidation bases are colorless or weakly colored compounds which, in combination with oxidizing products, can give rise, by an oxidative coupling process, to colored compounds.

It is also known that it is possible to vary the shades obtained with these oxidation bases by combining them with couplers or coloring modifiers, the latter being chosen, for example from aromatic meta-diamines, meta-aminophenols, meta-diphenols and certain heterocyclic compounds, such as indole compounds.

The variety of the molecules employed as oxidation bases and couplers makes it possible to obtain a rich palette of colors.

The "permanent" coloring obtained by these oxidation dyes furthermore should satisfy a certain number of requirements. The oxidation dyes should be toxicologically safe. It should also be possible to obtain shades within the desired intensity, and the oxidation dyes should behave well in the face of external agents, such as light, bad weather, washing, permanent waving, perspiration and rubbing.

The dyes should be able to cover white hair and be as non-selective as possible, i.e., make it possible to obtain the smallest possible differences in coloring along the same keratinous fiber, which is generally differentially sensitized (i.e., damaged) between its tip and its root.

It is already known to use aminopyrazolopyridine oxidation bases for the dyeing of keratinous fibers, for example, the aminopyrazolopyridine oxidation bases described in French Application Publication No. 2 801 308. These bases make it possible to obtain varied shades.

Furthermore, the use of dyeing compositions employing polyol solvents is known, for example, in French Application Publication No. 2 886 139.

SUMMARY OF THE INVENTION

Thus, one aspect of the present disclosure is a dyeing composition for coloring hair that exhibits enhanced dyeing properties in terms of power, selectivity and resistance to external agents.

DETAILED DESCRIPTION OF THE INVENTION

For example, one aspect of the present disclosure is a composition for dyeing keratinous fibers comprising, in an appropriate dyeing medium, at least one aminopyrazolopyridine oxidation base chosen from those of formula (I):

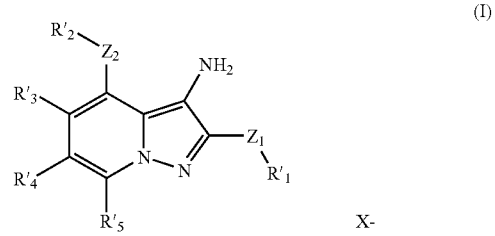

wherein:

$Z_1$ and $Z_2$ are each independently chosen from:
a simple covalent bond,
divalent radicals chosen from:
—O(CH$_2$)$_p$— radicals, wherein p is an integer ranging from 0 to 6, and
—NR'$_6$(CH$_2$)$_q$(C$_6$H$_4$)$_t$— radicals, wherein q is an integer ranging from 0 to 6, t is 0 or 1, and R'$_6$ is chosen from a hydrogen atom and $C_1$-$C_6$ alkyl radicals optionally substituted by at least one hydroxyl group, and
when R'$_1$ is a methyl radical, $Z_1$ can also be chosen from —S—, —SO— and —SO$_2$— radicals;

R'$_1$ and R'$_2$ are each independently chosen from:
a hydrogen atom,
optionally substituted $C_1$-$C_{10}$ alkyl radicals, optionally interrupted by a heteroatom or a group chosen from O, N, Si, S, SO and SO$_2$,
halogen atoms,
SO$_3$H radicals,
saturated, unsaturated, aromatic, substituted and unsubstituted 5- to 8-membered rings optionally comprising at least one heteroatom or group chosen from N, O, S, SO$_2$ and —CO—, it being possible for the ring to be cationic and/or substituted by a cationic radical,
—N$^+$R$_{17}$R$_{18}$R$_{19}$ groups, wherein R$_{17}$, R$_{18}$ and R$_{19}$ are independently chosen from linear and branched $C_1$-$C_5$ alkyl radicals which are optionally substituted by at least one hydroxyl group, and
when $Z_1$ is a covalent bond, then R'$_1$ can also be chosen from optionally substituted $C_1$-$C_6$ alkylcarbonyl radicals, and —O—CO—R, —CO—O—R, NR—CO—R' and —CO—NRR' radicals, wherein R and R' are each independently chosen from a hydrogen atom and optionally substituted $C_1$-$C_6$ alkyl radicals, and
when $Z_2$ is a covalent bond, then R'$_2$ can also be chosen from optionally substituted $C_1$-$C_6$ alkylcarbonyl radicals, and —O—CO—R', —CO—O—R', NR—CO—R' and —CO—NRR' radicals, wherein R and R' are each independently chosen from a hydrogen atom and optionally substituted $C_1$-$C_6$ alkyl radicals;

$R'_3$, $R'_4$ and $R'_5$ are each independently chosen from:
a hydrogen atom,
hydroxyl radicals,
$C_1$-$C_6$ alkoxy radicals,
$C_1$-$C_6$ alkylthio radicals,
amino radicals,
monoalkylamino radicals,
$C_1$-$C_6$ dialkylamino radicals wherein the alkyl radicals can form, with the nitrogen atom to which they are attached, a saturated or unsaturated, aromatic or non-aromatic 5- to 8-membered heterocycle which may comprise at least one heteroatom or group chosen from N, O, S, $SO_2$ and CO, it being possible for the heterocycle to be cationic and/or substituted by a cationic radical,
optionally substituted $C_1$-$C_6$ alkylcarbonyl radicals,
—O—CO—R, —CO—O—R, NR—CO—R' and —CO—NRR' radicals wherein R and R' are defined as above,
halogen atoms,
—$NHSO_3H$ radicals,
optionally substituted $C_1$-$C_4$ alkyl radicals, and
saturated, unsaturated, aromatic and optionally substituted carbon rings,
it being possible for $R'_3$, $R'_4$ and $R'_5$ to form, in pairs, a ring which is optionally partially saturated;

X— is chosen from electronegative ions or groups of ions which make it possible for the compound of formula (I) to be electronegative;

wherein it is understood that at least one of the groups $R'_1$ and $R'_2$ is chosen from cationic radicals;

at least one coupler; and at least one $C_4$-$C_{30}$ polyol comprising a saturated or unsaturated, linear, branched or cyclic hydrocarbon chain comprising at least two-hydroxyl functions, wherein the chain and its branches are optionally substituted by at least one other substituent chosen from carboxyl, amino, halogen and $C_6$-$C_{30}$ aryl groups; polyethylene glycols comprising 4, 6 or 7 ethylene units, and dipropylene glycol.

Another aspect of the present disclosure is a dyeing method employing the dyeing composition as described herein.

Yet another aspect is the use of the dyeing composition as disclosed herein for the dyeing of keratinous fibers, for example human keratinous fibers, such as the hair.

The dyeing composition as disclosed herein makes it possible, for example, to obtain a composition for the dyeing of keratinous fibers which is suitable for use in oxidation dyeing and which makes it possible to obtain a coloring with varied, powerful, attractive and non-selective shades which are highly resistant to the various attacks to which hair may be subjected, such as shampoos, light, sweat and permanent deformations.

Unless indicated otherwise, the end points encompassing a range of values are included in that range.

As disclosed herein, "alkyl" is understood to mean a linear or branched carbon chain comprising from 1 to 4 carbon atoms which is optionally substituted by at least one heterocycle or by at least one group chosen from phenyl groups, halogen atoms, such as chlorine, bromine, iodine and fluorine, hydroxyl radicals, alkoxy radicals, amino radicals, carbonyl radicals, carboxamido radicals, sulfonyl radicals, —$CO_2H$, —$SO_3H$, —$PO_3H_2$, —$PO_4H_2$, and —$NHSO_3H$ radicals, sulfonamido radicals, mono($C_1$-$C_4$)alkylamino radicals, tri($C_1$-$C_4$)alkylammonium radicals, and di($C_1$-$C_4$)alkylamino radicals wherein the two alkyl groups can optionally form, together with the nitrogen atom of the di($C_1$-$C_4$)alkylamino group to which they are bonded, a ring which can be interrupted by at least one atom chosen from nitrogen, oxygen and sulfur atoms.

As disclosed herein, "alkoxy" is understood to mean a linear or branched O-carbon chain comprising from 1 to 4 carbon atoms which is optionally substituted by at least one group chosen from heterocycles, halogen atoms, such as chlorine, bromine, iodine and fluorine, hydroxyl radicals, amino radicals, carbonyl radicals, carboxamido radicals, sulfonyl radicals, —$CO_2H$, —$SO_3H$, —$PO_3H_2$, —$PO_4H_2$, and —$NHSO_3H$ radicals, sulfonamido radicals, mono($C_1$-$C_4$) alkylamino radicals, tri($C_1$-$C_4$)alkylammonium radicals, and di($C_1$-$C_4$)alkylamino radicals wherein the two alkyl groups can optionally form, together with the nitrogen atom of the di($C_1$-$C_4$)alkylamino group to which they are bonded, a ring which can be interrupted by at least one atom chosen from nitrogen, oxygen and sulfur atoms.

As disclosed herein, "heterocycle" is understood to mean a 5-, 6-, 7- or 8-membered aromatic or non-aromatic ring comprising from 1 to 3 heteroatoms chosen from nitrogen, sulfur and oxygen atoms. These heterocycles can be fused to other heterocycles or to a phenyl group. They can be substituted by halogen atoms, ($C_1$-$C_4$)alkyl radicals, ($C_1$-$C_4$)alkoxy radicals hydroxyl radicals, amino radicals, ($C_1$-$C_4$)alkylamino radicals, and di($C_1$-$C_4$)alkylamino radicals wherein the two alkyl groups can optionally form, together with the nitrogen atom to which they are bonded, a ring which can be interrupted by at least one atom chosen from nitrogen, oxygen and sulfur atoms. In addition, these heterocycles can be quaternized by a ($C_1$-$C_4$)alkyl radical.

Non-limiting mention may be made of fused heterocycles such as thiadiazole, triazole, isoxazole, oxazole, azaphosphole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, aziridine, 3-(2-hydroxyethyl)benzothiazol-3-ium and 1-(2-hydroxyethyl)pyridinium.

As disclosed herein, "phenyl" is understood to mean a phenyl radical which is unsubstituted or substituted by at least one radical chosen from cyano, carbonyl, carboxamido, sulfonyl, —$CO_2H$, —$SO_3H$, —$PO_3H_2$, —$PO_4H_2$, hydroxyl, amino, mono($C_1$-$C_4$)alkylamino and di($C_1$-$C_4$)alkylamino radicals wherein the two alkyl groups can optionally form, together with the nitrogen atom to which they are bonded, a ring which can be interrupted by at least one atom chosen from nitrogen, oxygen and sulfur atoms.

As disclosed herein, "cationic ring" or "cationic heterocycle" is understood to mean a ring comprising at least one quaternary ammonium group.

Examples of radicals of the —$N^+R_{17}R_{18}R_{19}$ type that may be used in the present disclosure include, but are not limited to, trimethylammonium, triethylammonium, dimethylethylammonium, diethylmethylammonium, diisopropylmethylammonium, diethylpropylammonium, (β-hydroxyethyl)diethylammonium, di(β-hydroxyethyl)methyl-ammonium and tri(β-hydroxyethyl)ammonium radicals.

Non-limiting examples of cationic heterocycles that are suitable for the present disclosure include imidazolium, pyridinium, piperazinium, pyrrolidinium, morpholinium, pyrimidinium, thiazolium, benzimidazolium, benzothiazolium, oxazolium, benzotriazolium, pyrazolium, triazolium and benzoxazolium heterocycles.

The compounds of formula (I) can optionally be salified with strong inorganic acids, such as, but not limited to, HCl, HBr, $H_1$, $H_2SO_4$, $H_3PO_4$, and organic acids, such as, but not limited to, acetic acid, lactic acid, tartaric acid, citric acid, succinic acid, benzenesulfonic acid, para-toluenesulfonic acid, formic acid and methanesulfonic acid.

If the compounds of formula (I) comprise anionic groups, such as —$CO_2H$, —$SO_3H$, —$PO_3H_2$ and —$PO_4H_2$ groups, they can be salified by alkali metal or alkaline earth metal hydroxides, such as, but not limited to, sodium hydroxide, potassium hydroxide, aqueous ammonia and organic amines.

The compounds of formula (I) can also be in the form of solvates, for example, but not limited to, a hydrate or a solvate of a linear or branched alcohol, such as ethanol and isopropanol.

As disclosed herein, "derivative of formula (I)" is understood to mean all mesomeric or isomeric forms.

Mention may be made, as non-limiting examples of derivatives of formula (I), of the following compounds, wherein $X^-$ is as defined above:

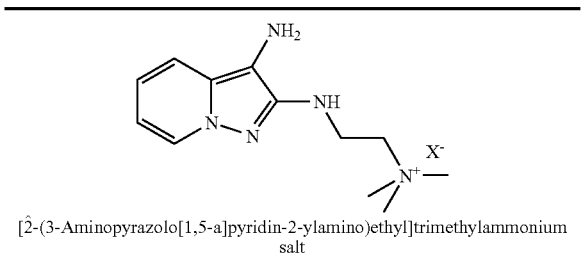

[2-(3-Aminopyrazolo[1,5-a]pyridin-2-ylamino)ethyl]trimethylammonium salt

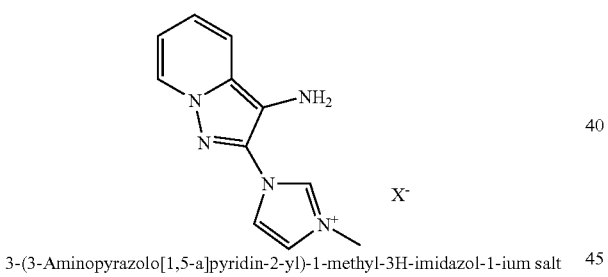

3-(3-Aminopyrazolo[1,5-a]pyridin-2-yl)-1-methyl-3H-imidazol-1-ium salt

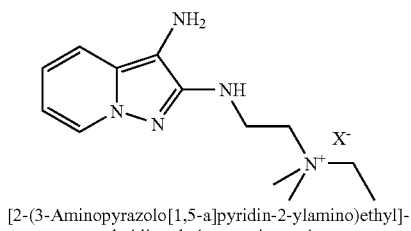

[2-(3-Aminopyrazolo[1,5-a]pyridin-2-ylamino)ethyl]-ethyldimethylammonium salt

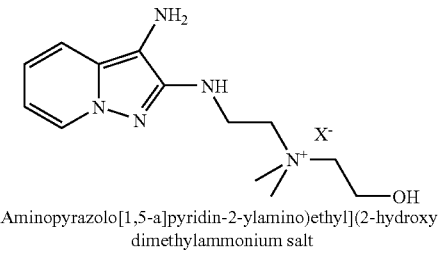

[2-(3-Aminopyrazolo[1,5-a]pyridin-2-ylamino)ethyl](2-hydroxyethyl)-dimethylammonium salt -continued

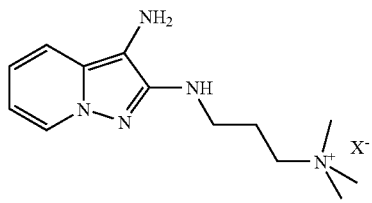

[3-(3-Aminopyrazolo[1,5-a]pyridin-2-ylamino)propyl]trimethylammonium salt

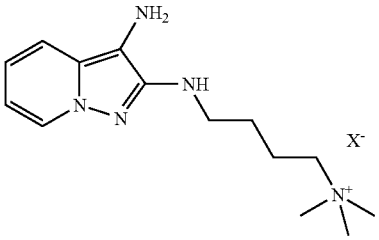

[4-(3-Aminopyrazolo[1,5-a]pyridin-2-ylamino)butyl]-trimethylammonium salt

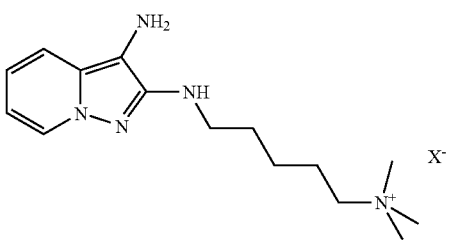

[5-(3-Aminopyrazolo[1,5-a]pyridin-2-ylamino)pentyl]trimethylammonium salt

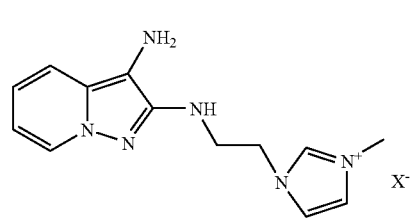

3-[2-(3-Aminopyrazolo[1,5-a]pyridin-2-ylamino)ethyl]-1-methyl-3H-imidazol-1-ium salt

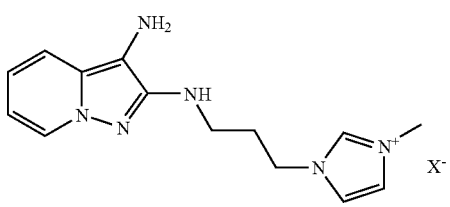

3-[3-(3-Aminopyrazolo[1,5-a]pyridin-2-ylamino)propyl]-1-methyl-3H-imidazol-1-ium salt

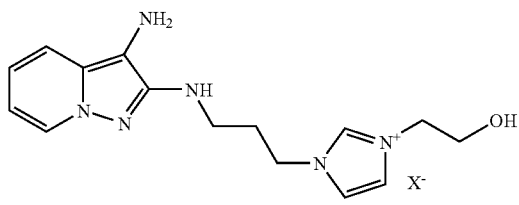

3-[3-(3-Aminopyrazolo[1,5-a]pyridin-2-ylamino)propyl]-1-(2-hydroxyethyl)-3H-imidazol-1-ium salt

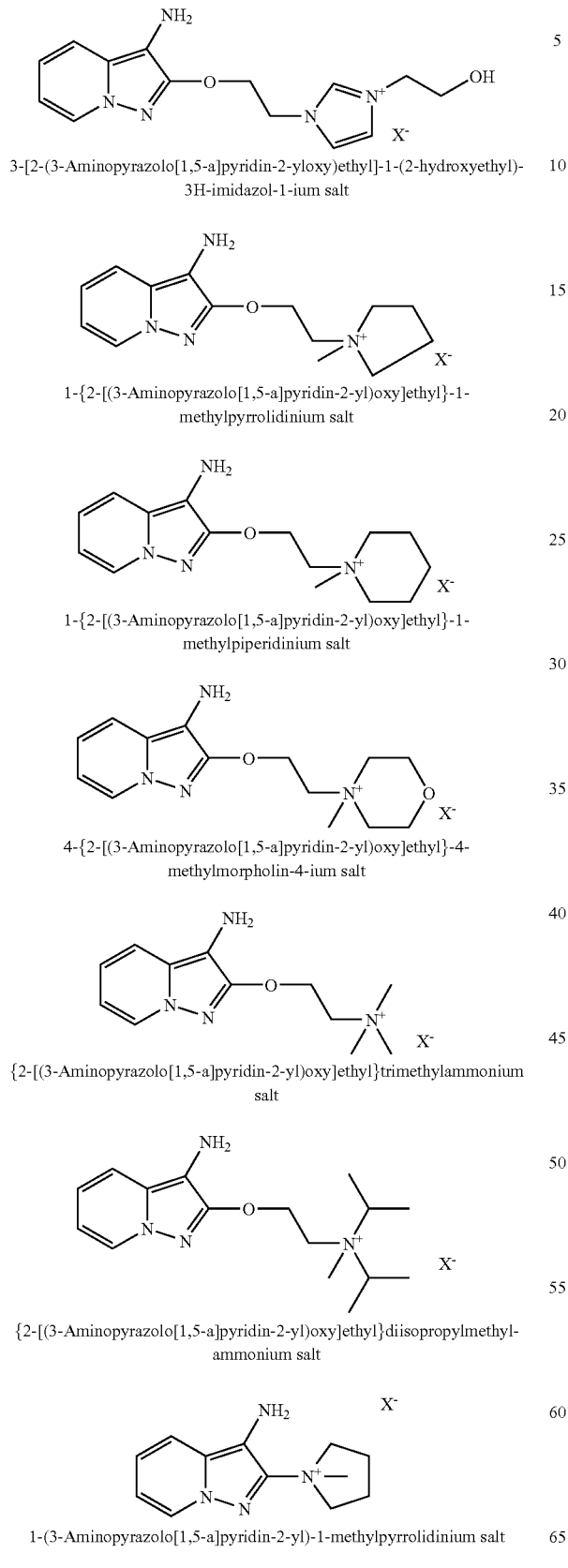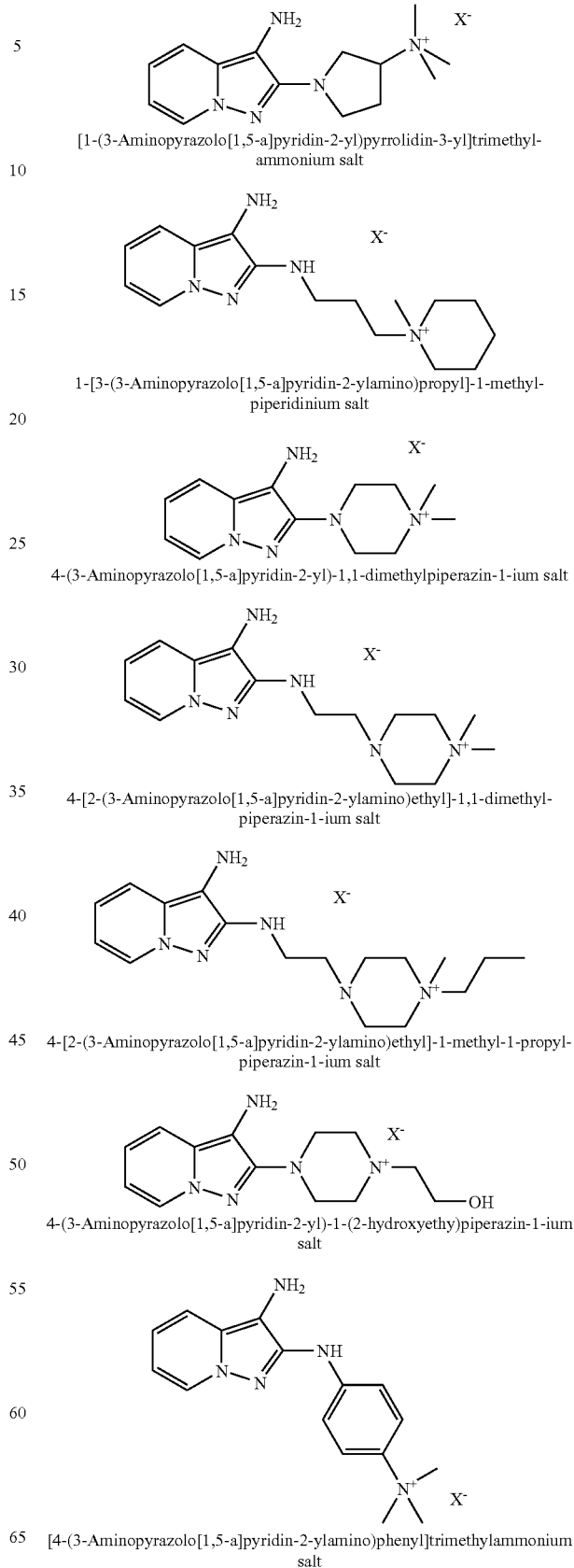

-continued

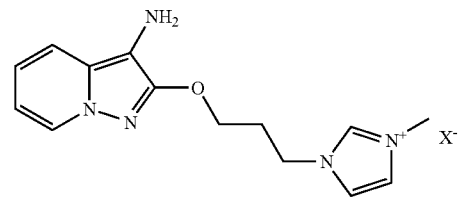

3-[3-(3-Aminopyrazolo[1,5-a]pyridin-2-yloxy)propyl]-1-methyl-3H-imidazol-1-ium salt

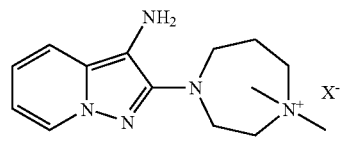

4-(3-Aminopyrazolo[1,5-a]pyridin-2-yl)-1,1-dimethyl-1,4-diazepan-1-ium salt

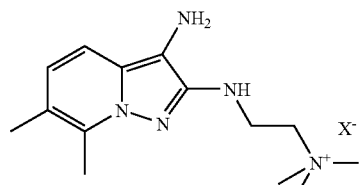

[2-(3-Amino-6,7-dimethylpyrazolo[1,5-a]pyridin-2-ylamino)ethyl]-trimethylammonium salt

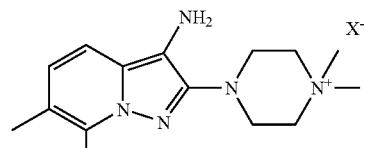

4-(3-Amino-6,7-dimethylpyrazolo[1,5-a]pyridin-2-yl)-1,1-dimethyl-piperazin-1-ium salt

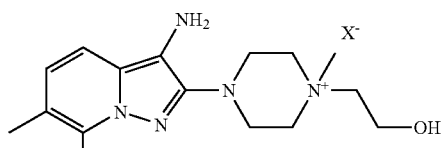

4-(3-Amino-6,7-dimethylpyrazolo[1,5-a]pyridin-2-yl)-1-(2-hydroxyethyl)-1-methylpiperazin-1-ium salt

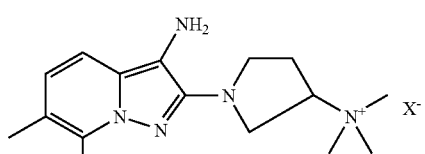

[1-(3-Amino-6,7-dimethylpyrazolo[1,5-a]pyridin-2-yl)pyrrolidin-3-yl]-trimethylammonium salt

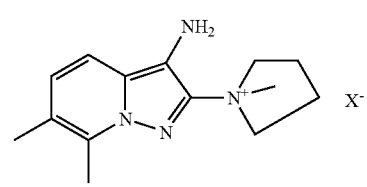

1-(3-Amino-6,7-dimethylpyrazolo[1,5-a]pyridin-2-yl)-1-methyl-pyrrolidinium salt

-continued

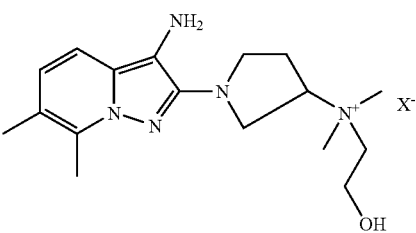

[1-(3-Amino-6,7-dimethylpyrazolo[1,5-a]pyridin-2-yl)pyrrolidin-3-yl]-(2-hydroxyethyl)dimethylammonium salt

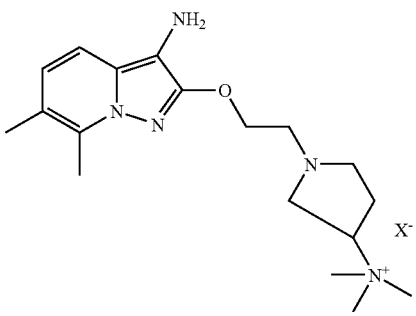

{1-[2-(3-Amino-6,7-dimethylpyrazolo[1,5-a]pyridin-2-yloxy)ethyl]-pyrrolidin-3-yl}trimethylammonium salt

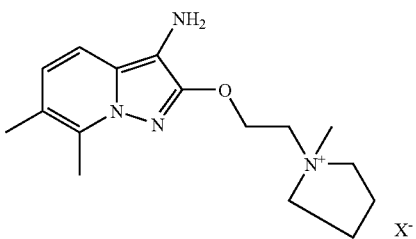

1-{2-[(3-Amino-6,7-dimethylpyrazolo[1,5-a]pyridin-2-yl)oxy]ethyl}-1-methylpyrrolidinium salt

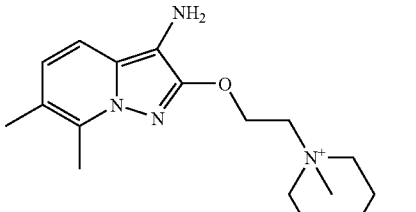

1-{2-[(3-Amino-6,7-dimethylpyrazolo[1,5-a]pyridin-2-yl)oxy]ethyl}-1-methylpiperidinium salt

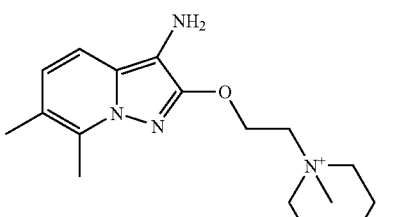

4-{2-[(3-Amino-6,7-dimethylpyrazolo[1,5-a]pyridin-2-yl)oxy]ethyl}-4-methylmorpholin-4-ium salt -continued

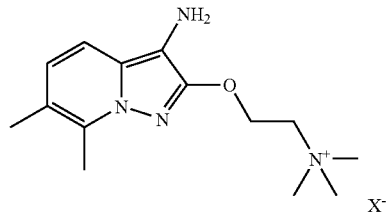

{2-[(3-Amino-6,7-dimethylpyrazolo[1,5-a]pyridin-2-yl)oxy]ethyl}-trimethylammonium salt

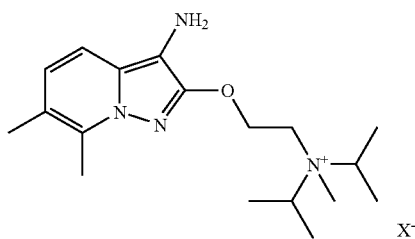

{2-[(3-Amino-6,7-dimethylpyrazolo[1,5-a]pyridin-2-yl)oxy]ethyl}-diisopropylmethylammonium salt

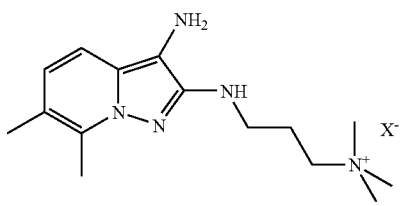

[3-(3-Amino-6,7-dimethylpyrazolo[1,5-a]pyridin-2-ylamino)propyl]-trimethylammonium salt

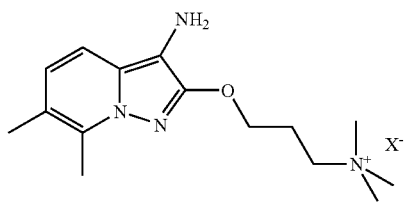

[3-(3-Amino-6,7-dimethylpyrazolo[1,5-a]pyridin-2-yloxy)propyl]-trimethylammonium salt

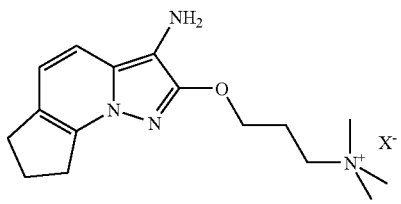

[3-(3-Amino-7,8-dihydro-6H-cyclopenta[e]pyrazolo[1,5-a]pyridin-2-yloxy)propyl]trimethylammonium salt

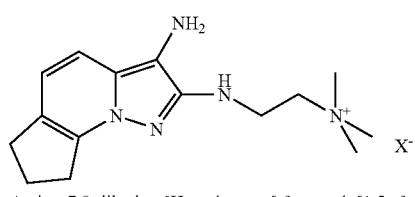

{2-[(3-Amino-7,8-dihydro-6H-cyclopenta[e]pyrazolo[1,5-a]pyridin-2-yl)amino]ethyl}trimethylammonium salt -continued

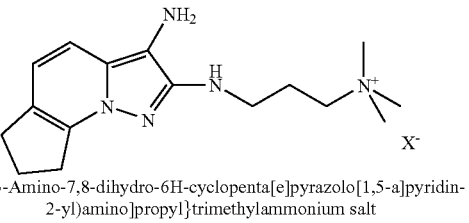

{3-[(3-Amino-7,8-dihydro-6H-cyclopenta[e]pyrazolo[1,5-a]pyridin-2-yl)amino]propyl}trimethylammonium salt

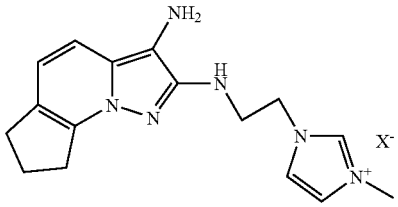

1-{2-[(3-Amino-7,8-dihydro-6H-cyclopenta[e]pyrazolo[1,5-a]pyridin-2-yl)amino]ethyl}-3-methyl-1H-imidazol-3-ium salt

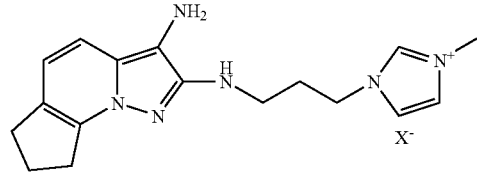

1-{3-[(3-Amino-7,8-dihydro-6H-cyclopenta[e]pyrazolo[1,5-a]pyridin-2-yl)amino]propyl}-3-methyl-1H-imidazol-3-ium salt

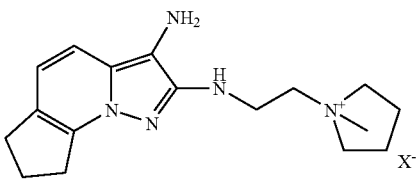

1-{2-[(3-Amino-7,8-dihydro-6H-cyclopenta[e]pyrazolo[1,5-a]pyridin-2-yl)amino]ethyl}-1-methylpyrrolidinium salt

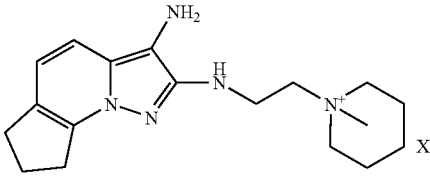

1-{2-[(3-Amino-7,8-dihydro-6H-cyclopenta[e]pyrazolo[1,5-a]pyridin-2-yl)amino]ethyl}-1-methylpiperidinium salt

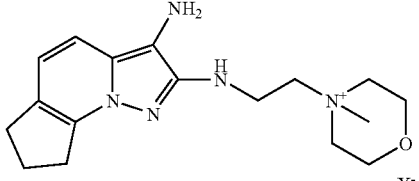

4-{2-[(3-Amino-7,8-dihydro-6H-cyclopenta[e]pyrazolo[1,5-a]pyridin-2-yl)amino]ethyl}-4-methylmorpholin-4-ium salt

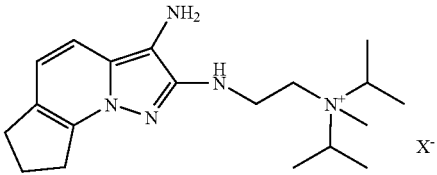

-continued

{2-[(3-Amino-7,8-dihydro-6H-cyclopenta[e]pyrazolo[1,5-a]pyridin-2-yl)amino]ethyl}diisopropylmethylammonium salt

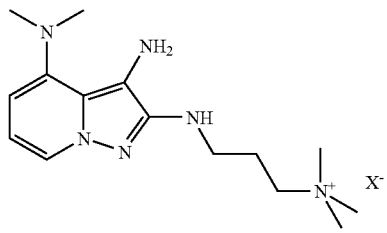

[3-(3-Amino-4-(dimethylamino)pyrazolo[1,5-a]pyridin-2-ylamino)propyl]-trimethylammonium salt

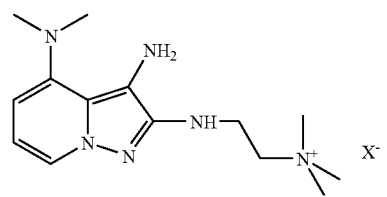

[2-(3-Amino-4-(dimethylamino)pyrazolo[1,5-a]pyridin-2-ylamino)ethyl]-trimethylammonium salt

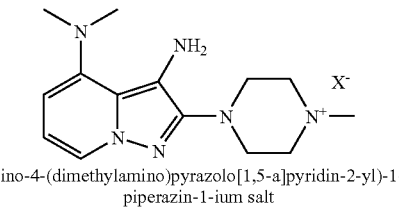

4-(3-Amino-4-(dimethylamino)pyrazolo[1,5-a]pyridin-2-yl)-1-methyl-piperazin-1-ium salt

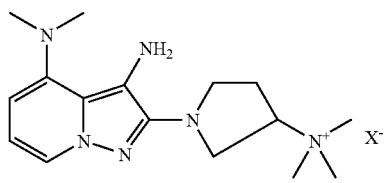

[1-(3-Amino-4-(dimethylamino)pyrazolo[1,5-a]pyridin-2-yl)pyrrolidin-3-yl]trimethylammonium salt

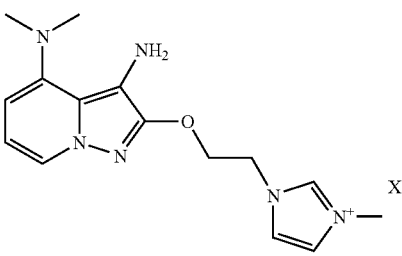

3-[2-(3-Amino-4-(dimethylamino)pyrazolo[1,5-a]pyridin-2-yloxy)ethyl]-1-methyl-3H-imidazol-1-ium salt

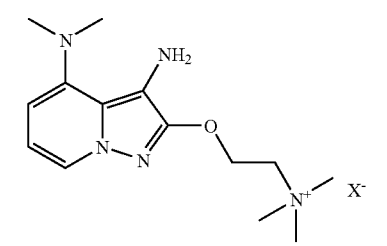

[2-(3-Amino-4-(dimethylamino)pyrazolo[1,5-a]pyridin-2-yloxy)ethyl]-trimethylammonium salt -continued

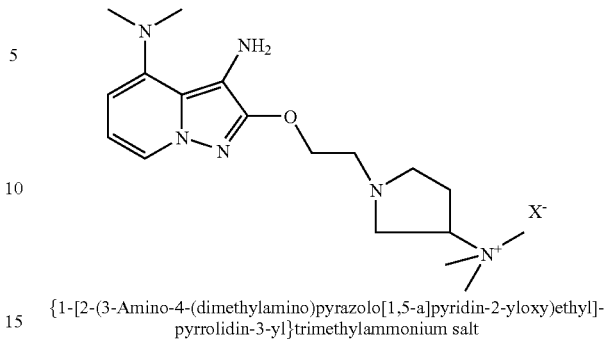

{1-[2-(3-Amino-4-(dimethylamino)pyrazolo[1,5-a]pyridin-2-yloxy)ethyl]-pyrrolidin-3-yl}trimethylammonium salt

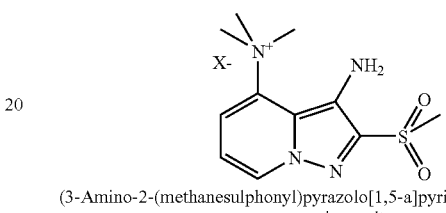

(3-Amino-2-(methanesulphonyl)pyrazolo[1,5-a]pyridin-4-yl)-trimethyl-ammonium salt

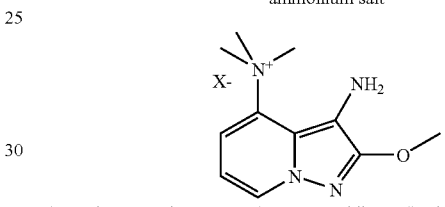

(3-Amino-2-methoxypyrazolo[1,5-a]pyridin-4-yl)-trimethylammonium salt

The nature of the counter-ion is not determining with regard to the dyeing power of the compounds of formula (I).

According to one embodiment of the disclosure, when $R'_1$ or $R'_2$ are heterocycles, they are cationic heterocycles or heterocycles substituted by a cationic radical. Non-limiting mention may be made of imidazoles substituted by a quaternary ammonium radical or imidazoliums, piperazines substituted by a quaternary ammonium radical and piperaziniums, pyrrolidines substituted by a quaternary ammonium radical and pyrrolidiniums, and diazepanes substituted by a quaternary ammonium radical and diazepaniums.

According to another embodiment of the disclosure, $R'_1$ or $R'_2$ are —$N^+R_{17}R_{18}R_{19}$ groups, wherein $R_{17}$, $R_{18}$ and $R_{19}$ are chosen from linear and branched $C_1$-$C_5$ alkyl radicals which are optionally substituted by at least one hydroxyl group, such as trialkylammonium, tri(hydroxyalkyl)ammonium, (hydroxyalkyl)dialkylammonium and di(hydroxyalkyl)alkylammonium.

The $R'_3$, $R'_4$ and $R'_5$ radicals can independently be chosen from a hydrogen atom and optionally substituted $C_1$-$C_4$ alkyl radicals, for example methyl, ethyl, hydroxyethyl, aminoethyl, propyl and butyl radicals. According to at least one embodiment of the present disclosure, $R'_3$, $R'_4$ and $R'_5$ are independently chosen from a hydrogen atom and $C_1$-$C_4$ alkyl radicals.

In at least one embodiment, $R'_4$ and $R'_5$ together, form a partially saturated or unsaturated, optionally substituted 5- or 6-membered ring, for example a cyclopentene or cyclohexene.

According to another aspect of the disclosure, the at least one compound of formula (I) is chosen from those of formula (I'):

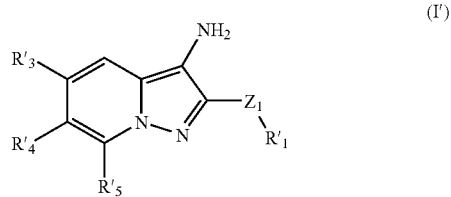

(I')

wherein $Z_1$, $R'_1$, $R'_3$, $R'_4$ and $R'_5$ are as defined above.

In one embodiment, $Z_1$ is chosen from a covalent bond, —$NR'_6(CH_2)_q$— radicals and —$O(CH_2)_p$— radicals and $R'_1$ is a cationic radical.

The at least one oxidation base of the present disclosure can be present in an amount ranging from 0.001% to 10% by weight, such as between 0.005% to 6% by weight, relative to the total weight of the dyeing composition.

The dyeing composition as disclosed herein comprises at least one coupler conventionally used for the dyeing of keratinous fibers. Examples of the at least one coupler include, but are not limited to, meta-phenylenediamines, meta-aminophenols, meta-diphenols, naphthalene couplers, heterocyclic couplers and their addition salts.

Other suitable couplers may be chosen, by way of non-limiting example, from 2-methyl-5-aminophenol, 5-N-(O-hydroxyethyl)amino-2-methylphenol, 6-chloro-2-methyl-5-aminophenol, 3-aminophenol, 2,4-dichloro-3-aminophenol, 5-amino-4-chloro-o-cresol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane; 3-ureidoaniline, 3-ureido-1-dimethylaminobenzene, sesamol, 1-(β-hydroxyethylamino)-3,4-methylenedioxybenzene, α-naphthol, 2-methyl-1-naphthol, 1,5-dihydroxynaphthalene, 2,7-naphthalenediol, 1-acetoxy-2-methylnaphthalene, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 2,6-dihydroxy-3-4-dimethylpyridine, 3-amino-2-methylamino-6-methoxypyridine, 1-N-(β-hydroxyethyl)amino-3,4-methylenedioxybenzene, 2,6-bis(β-hydroxyethylamino)toluene, 3-methyl-1-phenyl-5-pyrazolone, and their acid addition salts.

The at least one coupler can be present in an amount ranging from 0.001% to 10% by weight, such as between 0.005% to 6% by weight, relative to the total weight of the dyeing composition.

The composition of the present disclosure may further comprise at least one additional oxidation base conventionally used in oxidation dyeing that are different from the at least one oxidation base of formula (I). By way of nonlimiting example, these additional oxidation bases may be chosen from para-phenylenediamines other than those described above, bis-phenylalkylenediamines, para-aminophenols, bis-para-aminophenols, ortho-aminophenols, heterocyclic bases other than the at least one oxidation base of formula (I), and their addition salts.

Suitable para-phenylenediamines include, by way of non-limiting example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylene-diamine, 2-fluoro-para-phenylenediamine, 2-isopropyl-para-phenylenediamine, N-(β-hydroxypropyl)-para-phenylenediamine, 2-hydroxymethyl-para-phenylene-diamine, N,N-dimethyl-3-methyl-para-phenylenediamine, N,N-(ethyl, β-hydroxyethyl)-para-phenylenediamine, N-(β, γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-aminotoluene, 3-hydroxy-1-(4'-aminophenyl)pyrrolidine and their acid addition salts.

According to one embodiment of the disclosure, the para-phenylenediamines are chosen from para-phenylenediamine, para-toluenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and their acid addition salts.

Useful bisphenylalkylenediamines include, by way of non-limiting example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and their acid addition salts.

Examples of para-aminophenols that may be used in the present disclosure include, but are not limited to para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-((β-hydroxyethyl)aminomethyl)phenol, 4-amino-2-fluorophenol, 1-hydroxy-4-(methylamino)benzene, 2,2'-methylenebis(4-aminophenol) and their acid addition salts.

Ortho-aminophenols that may be used, by way of non-limiting example, include 2-aminophenol, 2-amino-5-methylphenol, 2-amino-6-methylphenol, 5-acetamido-2-aminophenol and their acid addition salts.

According to the present disclosure, suitable heterocyclic bases include, but are not limiting to, pyridine derivatives, pyrimidine derivatives and pyrazole derivatives.

Non-limiting examples of pyridine derivatives include the pyridine derivatives described in British Patent Nos. 1 026 978 and 1 153 196, such as 2,5-diaminopyridine, 2-[(4-methoxyphenyl)amino]-3-aminopyridine, 2,3-diamino-6-methoxypyridine, 2-[(β-methoxyethyl)amino]-3-amino-6-methoxypyridine, 3,4-diaminopyridine and their acid addition salts.

Non-limiting mention may be made of useful pyrimidine derivatives, for example, the pyrimidine derivatives described in German Application Publication No. 2 359 399; Japanese Patent Nos. 88-169571 and 05-63124; European Application Publication No. 0 770 375 or International Patent Application No. 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine or 2,5,6-triaminopyrimidine, and pyrazolopyrimidine derivatives, such as those mentioned in French Patent Application No. 2 750 048 and pyrazolo[1,5-a]pyrimidine-3,7-diamine; 2,5-dimethylpyrazolo[1,5-a]-pyrimidine-3,7-diamine; pyrazolo[1,5-a]pyrimidine-3,5-diamine; 2,7-dimethyl-pyrazolo[1,5-a]pyrimidine-3,5-diamine; 3-aminopyrazolo[1,5-a]pyrimidin-7-ol; 3-aminopyrazolo[1,5-a]pyrimidine-5-ol; 2-(3-aminopyrazolo[1,5-a]pyrimidin-7-ylamino)ethanol, 2-(7-aminopyrazolo[1,5-a]pyrimidine-3-ylamino)ethanol, 2-[(3-aminopyrazolo[1,5-a]pyrimidin-7-yl) (2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-(imidazolylpropylamino)pyrazolo[1,5-a]pyrimidine and their acid addition salts, and their tautomeric forms, when a tautomeric equilibrium exists.

Other useful pyrazole derivatives include, but are not limited to, the compounds disclosed in German Application Publication Nos. 3 843 892, 4 133 957 and 195 43 988, International Patent Application Nos. WO 94/08969 and WO 94/08970, and French Application Publication No. 2 733 749 and 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxy-ethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole and their acid addition salts.

Non-limiting mention may also be made of the diaminopyrazolinones described in French Application Publication No. 2 886 137 and, in at least one embodiment of the present disclosure, 2,3-diamino-6,7-dihydro-1H,5H-pyrazol-1-one and its salts thereof may be used.

As disclosed herein, nonlimiting examples of the addition salts of the at least one additional oxidation base and the at least one coupler include the acid addition salts such as hydrochlorides, hydrobromides, sulfates, citrates, succinates, tartrates, lactates, tosylates, benzenesulfonates, phosphates and acetates, and the base addition salts such as sodium hydroxide, potassium hydroxide, aqueous ammonia, amines and alkanolamines.

The dyeing composition according to the present disclosure, can additionally comprise at least one direct dye which may, in at least one embodiment, be chosen from nitrobenzene dyes, azo direct dyes and methine direct dyes. These direct dyes can be nonionic, anionic or cationic in nature.

As disclosed herein, the dyeing composition comprises at least one $C_4$-$C_{30}$ polyol.

Examples of suitable $C_4$-$C_{30}$ polyols include, but are not limited to, branched and unbranched diols, such as 1,4-butanediol, 1,5-pentanediol, 1,6-hexanediol, neopentyl glycol (or 2,3-dimethyl-1,3-propanediol), 2,5-hexanediol, amylene glycol (or 2,4-pentanediol), hexylene glycol (or 2-methyl-2,4-pentanediol), isoprene glycol (or 3-methyl-1,3-butanediol), pinacol (or 2,3-dimethyl-2,3-butanediol), 1-methoxy-2,4-butanediol, 4-methoxy-1,2-butanediol, branched and unbranched triols, such as 1,2,4-butanetriol and 1,2,6-hexanetriol, polyethylene glycols comprising 4, 6 or 7 ethylene units, and dipropylene glycol.

In at least one embodiment of the present disclosure, the at least one $C_4$-$C_{30}$ polyol is chosen from $C_4$-$C_{15}$ polyols, such as hexylene glycol, neopentyl glycol and isoprene glycol.

In the dyeing composition according to the present disclosure, the at least one $C_4$-$C_{30}$ polyol is present in an amount ranging from 0.1% to 40% by weight, such as 0.5% to 20% by weight, relative to the total weight of the dyeing composition.

According to the present disclosure, the medium appropriate for dyeing, also known as dyeing vehicle, generally comprises water or a mixture of water and of at least one water-soluble liquid monoalcohol, for example lower $C_1$-$C_4$ alkanols, such as ethanol and isopropanol.

These water-soluble liquid monoalcohols can be present in an amount ranging from 1% to 40% by weight, for instance 5% to 30% by weight, relative to the total weight of the dyeing composition The dyeing composition in accordance with the present disclosure may also comprise at least one adjuvant conventionally used in compositions for dyeing the hair, such as, but not limited to, anionic, cationic, nonionic, amphoteric, zwitterionic surfactants and their mixtures; anionic, cationic, nonionic, amphoteric, zwitterionic polymers and their mixtures; inorganic and organic thickening agents, such as anionic, cationic, nonionic and amphoteric polymeric associative thickeners; antioxidants; penetration agents; sequestering agents; fragrances; buffers; dispersing agents; conditioning agents, for example, volatile and non-volatile, modified and unmodified silicones; film-forming agents; ceramides; preservatives; and opacifying agents.

The at least one adjuvant may be present in an amount ranging from 0.01% to 20% by weight, relative to the total weight of the dyeing composition.

It is to be understood that a person skilled in the art will take care to choose this or these optional additional compounds such that the beneficial properties intrinsically associated with the oxidation dyeing composition in accordance with the present disclosure are not, or not substantially, detrimentally affected by the envisaged addition.

The pH of the dyeing composition in accordance with the present disclosure may range from approximately 3 to 12, such as from approximately 5 to 11. The pH can be adjusted to the desired value with acidifying or basifying agents commonly used in the dyeing of keratinous fibers or alternatively with conventional buffering systems.

Examples of useful acidifying agents include, but are not limited to, inorganic and organic acids, such as hydrochloric acid, orthophosphoric acid, sulfuric acid, carboxylic acids, acetic acid, tartaric acid, citric acid, lactic acid and sulfonic acids.

Non-limiting mention may be made of suitable basifying agents, for example aqueous ammonia, alkaline carbonates, alkanolamines, such as mono-, di- and triethanolamines and their derivatives, sodium hydroxide, potassium hydroxide and the compounds of formula (II):

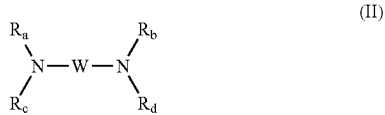

(II)

wherein W is chosen from a propylene residue optionally substituted by a hydroxyl group and $C_1$-$C_4$ alkyl radicals, and $R_a$, $R_b$, $R_c$ and $R_d$, are each independently chosen from a hydrogen atom, $C_1$-$C_4$ alkyl radicals and $C_1$-$C_4$ hydroxyalkyl radicals.

The dyeing composition as disclosed herein, may be in various forms, such as, but not limited to, liquids, creams and gels or in any other form appropriate for carrying out dyeing of keratinous fibers, such as human hair.

The method for dyeing keratinous fibers, in accordance with the present disclosure, comprises applying the dyeing composition, as disclosed herein, to the keratinous fibers in the presence of at least one oxidizing agent for a time sufficient to develop the desired coloring. The color can be developed at acidic, neutral or alkaline pH and in one embodiment, the color is developed at acidic pH. The at least one oxidizing agent can be added to the dyeing composition as disclosed herein only at the time of use or it can be employed in an oxidizing composition, applied simultaneously with or sequentially to the dyeing composition.

According to at least one embodiment of the present disclosure, the dyeing composition is mixed, for instance at the time of use, with a composition comprising, in a medium appropriate for dyeing, at least one oxidizing agent present in an amount sufficient to develop a coloring. The mixture obtained is subsequently applied to the keratinous fibers. After a setting time of approximately 3 to 50 minutes, for example approximately 5 to 30 minutes, the keratinous fibers are rinsed, washed with shampoo, rinsed again and then dried.

The at least one oxidizing agent conventionally used for the oxidation dyeing of keratinous fibers may be chosen from hydrogen peroxide, urea hydrogen peroxide, alkali metal bromates, persalts, such as perborates and persulfates, peracids and oxidase enzymes, such as peroxidases, 2-electron oxidoreductases, such as uricases, and 4-electron oxygenases, such as laccases. In at least one embodiment, hydrogen peroxide may be used.

The oxidizing composition can also include at least one adjuvant chosen from the various adjuvants conventionally used in compositions for the dyeing of the hair and as defined above.

The pH of the oxidizing composition comprising the at least one oxidizing agent is such that, after mixing with the dyeing composition, the pH of the resulting composition applied to the keratinous fibers may range from approximately 3 to 12, such as from 5 to 11. The pH may be adjusted to the desired value using acidifying or basifying agents commonly used in the dyeing of keratinous fibers and as defined above.

The ready-for-use composition which is finally applied to the keratinous fibers may be in various forms, such as liquids, creams and gels, or in any other form suitable for dyeing keratinous fibers such as human hair.

Another aspect of the present disclosure is a multicompartment dyeing device comprising, in at least one first compartment, at least one dyeing composition in accordance with the disclosure and in at least one second compartment, at least one oxidizing agent. This device can be equipped to allow the desired mixture to be deposited on the hair, such as the devices described, for example in French Application Publication No. 2 586 913.

According to the present disclosure, this device may make it possible to dye keratinous fibers by using a method, as disclosed herein, comprising mixing a dyeing composition comprising at least one oxidation base of formula (I), at least one coupler and at least one $C_4$-$C_{30}$ polyol according to the present disclosure with at least one oxidizing agent and then applying the mixture obtained to the keratinous fibers for a time sufficient to develop the desired coloring.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The following example serves to illustrate the an embodiment of the present disclosure without, however, exhibiting a limiting nature.

EXAMPLES

Dyeing Examples

Composition 1 was prepared with the following dyes (mol):

| Moles per 100 g of composition | Hydrochloride of 2-[(3-aminopyrazolo[1,5-a]pyridin-2-yl)amino]-N,N,N-trimethyl-ethanaminium chloride | 6-Hydroxy-benzomorpholine |
|---|---|---|
| Composition 1 | 0.01 | 0.01 | and introduced into the following medium:

| | |
|---|---|
| Mixture of $C_{18}$ to $C_{24}$ linear alcohols [$C_{18}$/$C_{20}$/$C_{22}$/$C_{24}$: 7/58/30/6 - alcohol content >95%] | 3 g |
| Mixture of $C_{18}$ to $C_{24}$ linear alcohols [$C_{18}$/$C_{20}$/$C_{22}$/$C_{24}$: 7/58/30/6 - alcohol content >95%] which are ethoxylated (30 EO) | 1 g |
| Ethoxylated stearyl alcohol (2 EO) | 4.5 g |
| Ethoxylated stearyl alcohol (21 EO) | 1.75 g |
| Crosslinked polyacrylic acid (CARBOPOL 980 from Goodrich) | 0.6 g |
| Oleic acid | 2.6 g |
| ACULYN 44 sold by Rohm & Haas | 1.4 g a.m. |
| Monoisopropanolamide of coconut acids | 3 g |
| Cationic polymer of formula W | 4 g a.m. |
| Hexylene glycol | 6 g |
| Sodium metabisulfite | 0.71 g |

-continued

| | |
|---|---|
| EDTA (ethylenediaminetetraacetic acid) | 0.2 g |
| tert-Butylhydroquinone | 0.3 g |
| Monoethanolamine | 1 g |
| Aqueous ammonia containing 20% NH$_3$ | 11 g |
| Fragrance | q.s. |
| Demineralized water | q.s. for 100 g |

A.M.: Active Material

Method of Application

The composition was mixed at the time of use with 1.5 times its volume of 25-volume aqueous hydrogen peroxide solution, the pH of which was 3.

The mixture produced was then applied to natural grey hair comprising 90% of white hairs in a proportion of 30 g per 3 g of hair for 30 min.

The hair was subsequently rinsed, washed with a standard shampoo and dried.

Results

The hair coloring was evaluated visually.

| | Level of tone 90% Natural White | Highlight 90% Natural White |
|---|---|---|
| Composition 1 | Blond | Green |

These shades were long-lasting and uniform.

Example 2

The following compositions were prepared:

1-{2-[(3-Aminopyrazolo[1,5-a]pyridin-2-yl)amino]ethyl}-3-methyl-1H-imidazol-3-ium hydrochloride 1.3 g (0.004 moles %)

2-Methyl 5-(2-hydroxyethyl)amino phenol 0.67 g (0.004 moles %)

sodium Metabisulfite 0.68 g

Ascorbic acid 0.3 g

Aqueous ammonia comprising 20% NH$_3$ 10 g

Solvents 6 g

Water q.s. for 100 g

Composition 2 (comparative): the solvent was ethanol

Composition 3 (present disclosure): the solvent was hexylene glycol

Method of Application

The compositions were mixed at the time of use with 1 time its weight of 20 volume hydrogen peroxide aqueous solution, pH of which was 3.

The resulting mixture was then applied to natural or permed grey hair comprising 90% of white hairs in a proportion of 20 g per 2 g of hair for 30 min.

The hair was then rinsed, washed with standard shampoo and dried.

Color Determination

The color on the hair was evaluated in the L*a*b* system, with a spectrophotometer SF600X of Datacolor (diffus, 8°): opening SAV, measure in SCI, UVI with illuminant D65.

According to this system, L* indicates the lightness. The lowest is the value of L*, the most intense is the color of the hair. The chromaticity coordinates are expressed by the parameters a* and b*, a* indicating the axis of red/green shades and b the axis of yellow/blue shades Selectivity of the Coloration The selectivity of the coloration is the variation of the color between natural colored hair and permed colored hair. Natural hair is representative of the nature of the hair at the tip and the permed hair is representative of the nature of the hair at the root.

The selectivity is measured by:

ΔE, which is the color variation between a natural colored lock and a permed colored lock, is obtained from the following formula:

$$\Delta E = \sqrt{(L^*-L_o^*)^2+(a^*-a_o^*)^2+(b^*-b_o^*)^2}$$

wherein L* indicates lightness and a* and b* are the chromaticity coordinates of the natural colored locks, whereas $L_o$* indicates the lightness and $a_o$* et $b_o$* are the chromaticity of the permed colored locks. A lower value of ΔE indicates lower selectivity of the coloration and, thus, better hair color.

The L*a*b* values obtained from the dyed natural or permed hair and the selectivity are reported in the following table.

| | Natural fibers after coloration | | | Permed fibers after coloration | | | |
|---|---|---|---|---|---|---|---|
| | L* | a* | b* | L* | a* | b* | Selectivity |
| Composition 2 | 19.8 | 9.3 | −14.1 | 17.4 | 4.7 | −7.8 | 8.2 |
| Composition 3 | 20.2 | 8.9 | −13.6 | 18.6 | 6.5 | −11 | 3.9 |

The results show that the selectivity for the comparative composition 2 is poorer than that obtained from the composition 3 (of the present disclosure).

What is claimed is:

1. A composition for dyeing keratinous fibers, comprising, in an appropriate dyeing medium:
at least one aminopyrazolopyridine oxidation base chosen from those of formula (I):

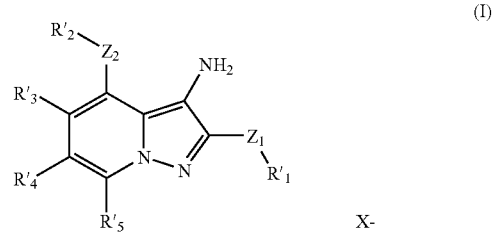

wherein:

$Z_1$ and $Z_2$ are each independently chosen from:
a simple covalent bond,
divalent radicals chosen from:
—O(CH$_2$)$_p$— radicals, wherein p is an integer ranging from 0 to 6, and
—NR'$_6$(CH$_2$)$_q$(C$_6$H$_4$)$_t$— radicals, wherein q is an integer ranging from 0 to 6, t is 0 or 1, and R'$_6$ is chosen from a hydrogen atom and $C_1$-$C_6$ alkyl radicals optionally substituted by at least one hydroxyl group, and when $R'_1$ is a methyl radical, $Z_1$ can also be chosen from divalent radicals —S—, —SO— and —$SO_2$—;

$R'_1$ and $R'_2$ are each independently chosen from:
a hydrogen atom,
optionally substituted $C_1$-$C_{10}$ alkyl radicals, optionally interrupted by a heteroatom or a group chosen from O, N, Si, S, SO and $SO_2$,
halogen atoms,
$SO_3H$ radicals,
saturated, unsaturated, aromatic, substituted and unsubstituted 5- to 8-membered ring optionally comprising at least one heteroatom or group chosen from N, O, S, $SO_2$ and —CO—, it being possible for the ring to be cationic and/or substituted by a cationic radical,
—$N^+R_{17}R_{18}R_{19}$ groups, wherein $R_{17}$, $R_{18}$ and $R_{19}$ are each independently chosen from linear and branched $C_1$-$C_5$ alkyl radicals which are optionally substituted by at least one hydroxyl group, and
when $Z_1$ is a covalent bond, then $R'_1$ can also be chosen from:
optionally substituted $C_1$-$C_6$ alkylcarbonyl radicals, and —O—CO—R, —CO—O—R, NR—CO—R' and —CO—NRR' radicals wherein R and R' are independently chosen from a hydrogen atom and optionally substituted $C_1$-$C_6$ alkyl radicals, and
when $Z_2$ is a covalent bond, then $R'_2$ can also be chosen from:
optionally substituted $C_1$-$C_6$ alkylcarbonyl radicals, and —O—CO—R, —CO—O—R, NR—CO—R' and —CO—NRR' radicals wherein R and R' are independently chosen from a hydrogen atom and optionally substituted $C_1$-$C_6$ alkyl radicals;
$R'_3$, $R'_4$ and $R'_5$ are each independently chosen from:
a hydrogen atom,
hydroxyl radicals,
$C_1$-$C_6$ alkoxy radicals,
$C_1$-$C_6$ alkylthio radicals,
amino radicals,
monoalkylamino radicals,
$C_1$-$C_6$ dialkylamino radicals wherein the alkyl radicals can form, with the nitrogen atom to which they are attached, a saturated or unsaturated, aromatic or non-aromatic 5- to 8-membered heterocycle which can comprise at least one heteroatom or group chosen from N, O, S, $SO_2$ and CO, it being possible for the heterocycle to be cationic and/or substituted by a cationic radical,
optionally substituted $C_1$-$C_6$ alkylcarbonyl radicals, —O—CO—R, —CO—O—R, NR—CO—R' and —CO—NRR' radicals wherein R and R' as defined above,
halogen atoms,
—$NHSO_3H$ radicals,
optionally substituted $C_1$-$C_4$ alkyl radicals, and
saturated, unsaturated, aromatic and optionally substituted carbon rings,
it being possible for $R'_3$, $R'_4$ to $R'_5$ to form, in pairs, a ring which is optionally partially saturated; and X— is chosen from electronegative ions or groups of ions; wherein it is understood that at least one of the groups $R'_1$ and $R'_2$ is chosen from cationic radicals;
at least one coupler; and
at least one $C_4$-$C_{30}$ polyol comprising a saturated or unsaturated, linear, branched or cyclic hydrocarbon chain comprising at least two hydroxyl functions, wherein the chain and its branches are optionally substituted by at least one other substituent chosen from carboxyl, amino, halogens, $C_6$-$C_{30}$ aryl groups, polyethylene glycols comprising 4, 6 or 7 ethylene units and dipropylene glycol.

2. The composition according to claim 1, wherein at least one of $Z_1$ and/or $Z_2$ is chosen from a covalent bond, —$NR'_6$ $(CH_2)_q$— radicals and —$O(CH_2)_p$— radicals, and $R'_1$ and/or $R'_2$ is a cationic radical.

3. The composition according to claim 2, wherein $R'_1$ or $R'_2$ is chosen from imidazoles substituted by a quaternary ammonium radical and imidazoliums, piperazines substituted by a quaternary ammonium radical and piperaziniums, pyrrolidines substituted by a quaternary ammonium radical and pyrrolidiniums, and diazepanes substituted by a quaternary ammonium radical and diazepaniums.

4. The composition according to claim 1, wherein $R'_1$ and $R'_2$ are independently chosen from a hydrogen atom, trialkylammonium groups, tri(hydroxyalkyl)ammonium groups, (hydroxyalkyl)dialkylammonium groups and di(hydroxyalkyl)alkylammonium groups.

5. The composition according to claim 1, wherein $R'_3$, $R'_4$ and $R'_5$ are independently chosen from a hydrogen atom and optionally substituted $C_1$-$C_4$ alkyl radicals.

6. The composition according to claim 1, wherein the at least one compound of formula (I) is chosen from those of formula (I'):

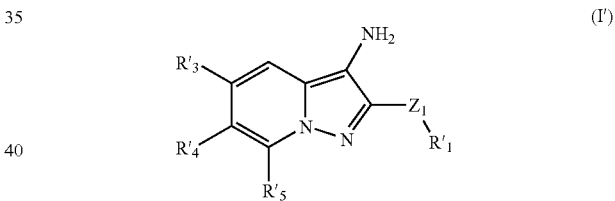

wherein $Z_1$, $R'_1$, $R'_3$, $R'_4$ and $R'_5$ are as defined in claim 1.

7. The composition according to claim 6, wherein $Z_1$ is chosen from a covalent bond, —$NR'_6(CH_2)_q$— radicals and $O(CH_2)_p$— radicals, and $R'_1$ is a cationic radical.

8. The composition according to claim 1, wherein the compound of formula (I) is chosen from:

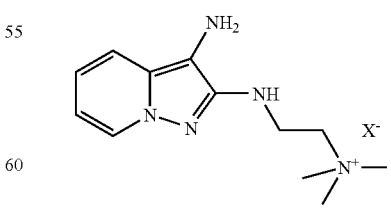

[2-(3-Aminopyrazolo[1,5-a]pyridin-2-ylamino)ethyl]trimethylammonium salt

-continued

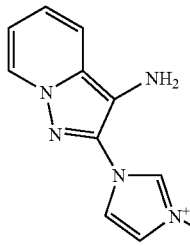

3-(3-Aminopyrazolo[1,5-a]pyridin-2-yl)-1-methyl-3H-imidazol-1-ium salt

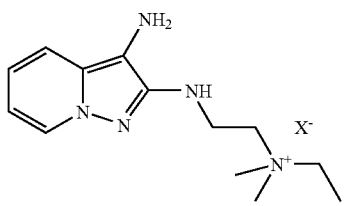

[2-(3-Aminopyrazolo[1,5-a]pyridin-2-ylamino)ethyl]ethyl-dimethylammonium salt

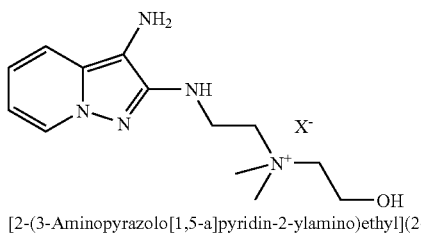

[2-(3-Aminopyrazolo[1,5-a]pyridin-2-ylamino)ethyl](2-hydroxyethyl)dimethylammonium salt

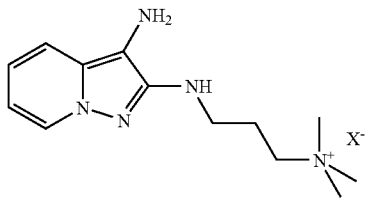

[3-(3-Aminopyrazolo[1,5-a]pyridin-2-ylamino)propyl]tri-methylammonium salt

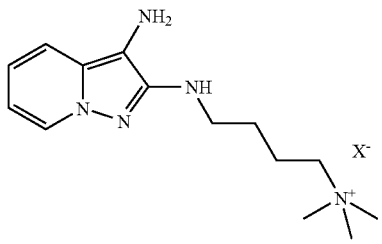

[4-(3-Aminopyrazolo[1,5-a]pyridin-2-ylamino)butyl]-tri-methylammonium salt

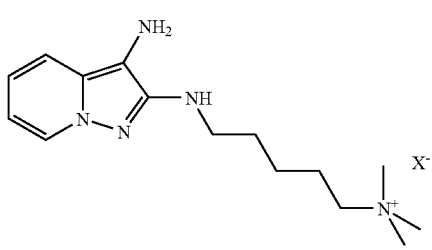

[5-(3-Aminopyrazolo[1,5-a]pyridin-2-ylamino)pentyl]tri-methylammonium salt

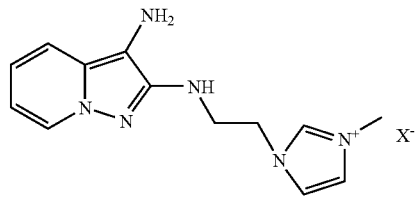

3-[2-(3-Aminopyrazolo[1,5-a]pyridin-2-ylamino)ethyl]-1-methyl-3H-imidazol-1-ium salt

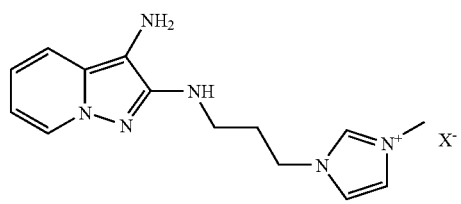

3-[3-(3-Aminopyrazolo[1,5-a]pyridin-2-ylamino)propyl]-1-methyl-3H-imidazol-1-ium salt

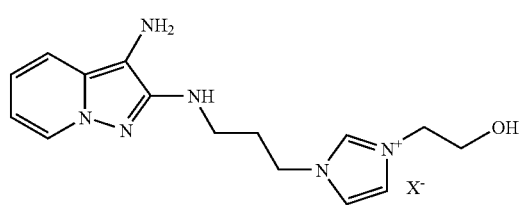

3-[3-(3-Aminopyrazolo[1,5-a]pyridin-2-ylamino)propyl]-1-(2-hydroxyethyl)-3H-imidazol-1-ium salt

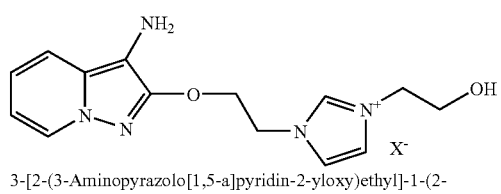

3-[2-(3-Aminopyrazolo[1,5-a]pyridin-2-yloxy)ethyl]-1-(2-hydroxyethyl)-3H-imidazol-1-ium salt

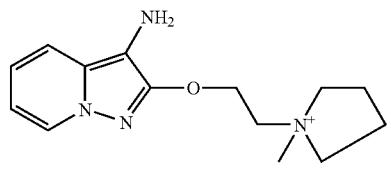

1-{2-[(3-Aminopyrazolo[1,5-a]pyridin-2-yl)oxy]ethyl}-1-methylpyrrolidinium salt

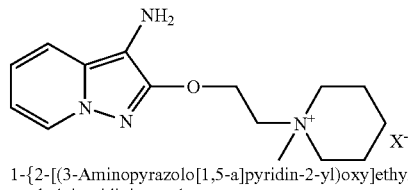

1-{2-[(3-Aminopyrazolo[1,5-a]pyridin-2-yl)oxy]ethyl}-1-methylpiperidinium salt

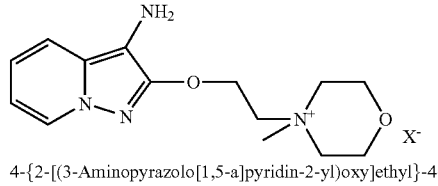

4-{2-[(3-Aminopyrazolo[1,5-a]pyridin-2-yl)oxy]ethyl}-4- methylmorpholin-4-ium salt

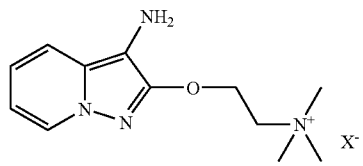

{2-[(3-Aminopyrazolo[1,5-a]pyridin-2-yl)oxy]ethyl}trimethylammonium salt

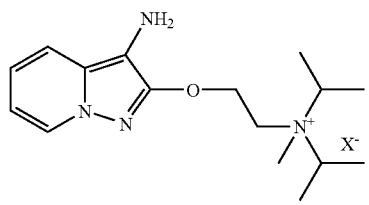

{2-[(3-Aminopyrazolo[1,5-a]pyridin-2-yl)oxy]ethyl}-diisopropylmethylammonium salt

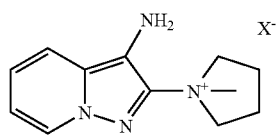

1-(3-Aminopyrazolo[1,5-a]pyridin-2-yl)-1-methylpyrrolidinium salt

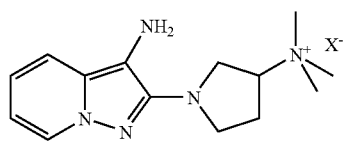

[1-(3-Aminopyrazolo[1,5-a]pyridin-2-yl)pyrrolidin-3-yl]trimethylammonium salt

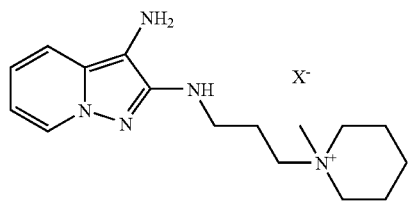

1-[3-(3-Aminopyrazolo[1,5-a]pyridin-2-ylamino)propyl]-1-methylpiperidinium salt

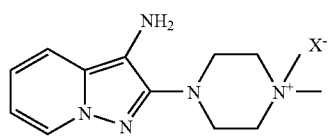

4-(3-Aminopyrazolo[1,5-a]pyridin-2-yl)-1,1-dimethylpiperazin-1-ium salt

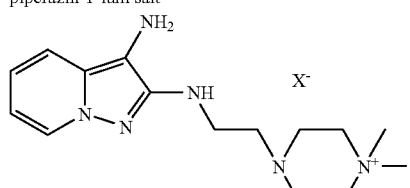

4-[2-(3-Aminopyrazolo[1,5-a]pyridin-2-ylamino)ethyl]-1,1-dimethylpiperazin-1-ium salt

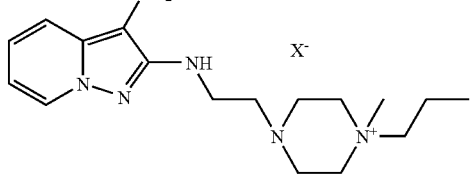

4-[2-(3-Aminopyrazolo[1,5-a]pyridin-2-ylamino)ethyl]-1-methyl-1-propylpiperazin-1-ium salt

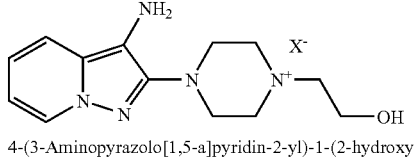

4-(3-Aminopyrazolo[1,5-a]pyridin-2-yl)-1-(2-hydroxyethyl)piperazin-1-ium salt

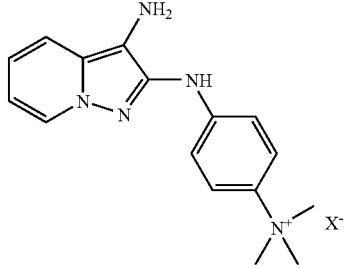

[4-(3-Aminopyrazolo[1,5-a]pyridin-2-ylamino)phenyl]-trimethylammonium salt

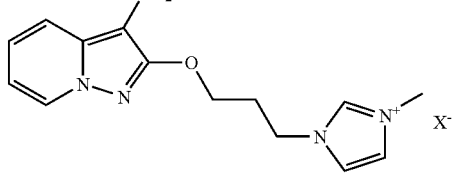

3-[3-(3-Aminopyrazolo[1,5-a]pyridin-2-yloxy)propyl]-1-methyl-3H-imidazol-1-ium salt

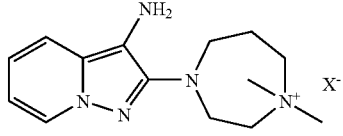

4-(3-Aminopyrazolo[1,5-a]pyridin-2-yl)-1,1-dimethyl-1,4-diazepan-1-ium salt

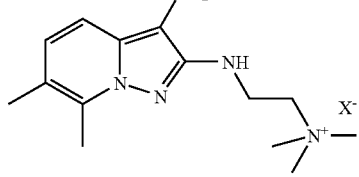

[2-(3-Amino-6,7-dimethylpyrazolo[1,5-a]pyridin-2-ylamino)ethyl]trimethylammonium salt -continued

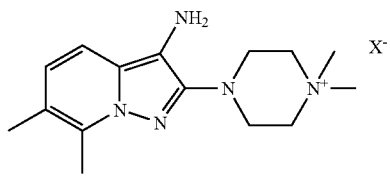

4-(3-Amino-6,7-dimethylpyrazolo[1,5-a]pyridin-2-yl)-1,1-dimethylpiperazin-1-ium salt

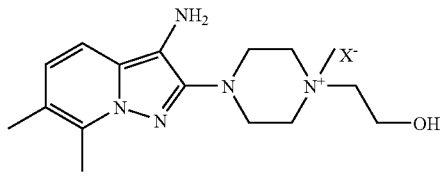

4-(3-Amino-6,7-dimethylpyrazolo[1,5-a]pyridin-2-yl)-1-(2-hydroxyethyl)-1-methylpiperazin-1-ium salt

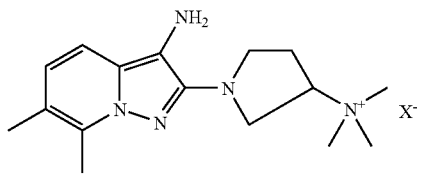

[1-(3-Amino-6,7-dimethylpyrazolo[1,5-a]pyridin-2-yl)pyrrolidin-3-yl]trimethylammonium salt

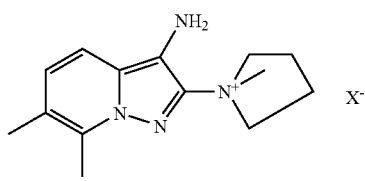

1-(3-Amino-6,7-dimethylpyrazolol[1,5-a]pyridin-2-yl)-1-methylpyrrolidinium salt

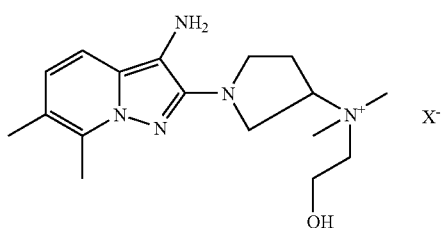

[1-(3-Amino-6,7-dimethylpyrazolo[1,5-a]pyridin-2-yl)pyrrolidin-3-yl](2-hydroxyethyl)dimethylammonium salt

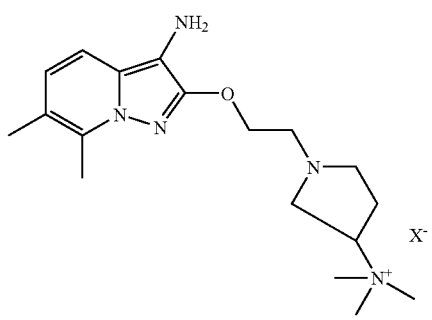

{1-[2-(3-Amino-6,7-dimethylpyrazolo[1,5-a]pyridin-2-yloxy)-ethyl]pyrrolidin-3-yl}trimethylammonium salt -continued

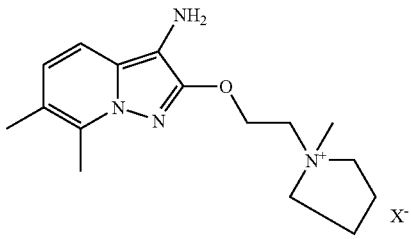

1-{2-[(3-Amino-6,7-dimethylpyrazolo[1,5-a]pyridin-2-yl)oxy]-ethyl}-1-methylpyrrolidinium salt

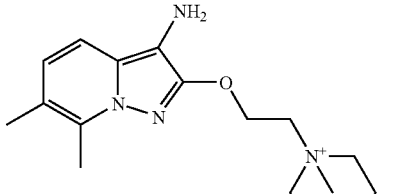

1-{2-[(3-Amino-6,7-dimethylpyrazolo[1,5-a]pyridin-2-yl)oxy]-ethyl}-1-methylpiperidinium salt

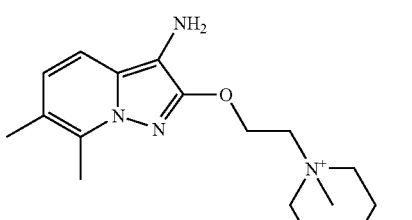

4-{2-[(3-Amino-6,7-dimethylpyrazolo[1,5-a]pyridin-2-yl)oxy]-ethyl}-4-methylmorpholin-4-ium salt

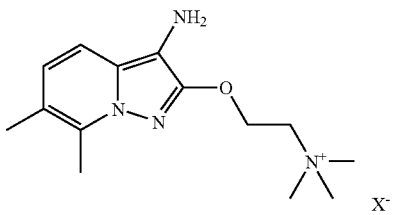

{2-[(3-Amino-6,7-dimethylpyrazolo[1,5-a]pyridin-2-yl)oxy]ethyl}trimethylammonium salt

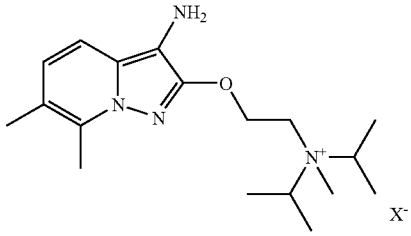

{2-[(3-Amino-6,7-dimethylpyrazolo[1,5-a]pyridin-2-yl)oxy]ethyl}diisopropylmethylammonium salt

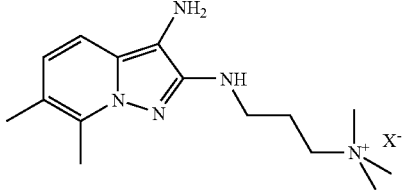

-continued

[3-(3-Amino-6,7-dimethylpyrazolo[1,5-a]pyridin-2-ylamino)propyl]trimethylammonium salt

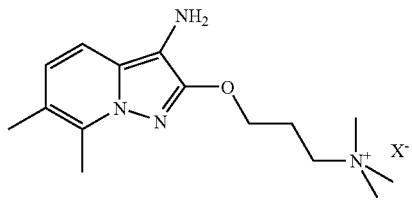

[3-(3-Amino-6,7-dimethylpyrazolo[1,5-a]pyridin-2-yloxy)propyl]trimethylammonium salt

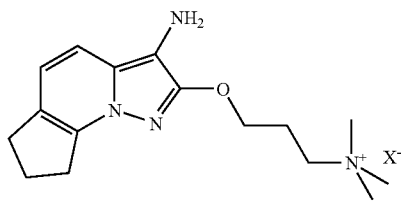

[3-(3-Amino-7,8-dihydro-6H-cyclopenta[e]pyrazolo[1,5-a]pyridin-2-yloxy)propyl]trimethylammonium salt

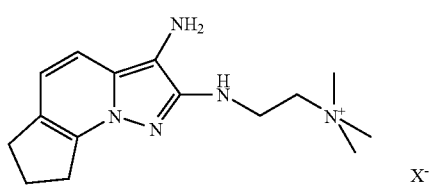

{2-[(3-Amino-7,8-dihydro-6H-cyclopenta[e]pyrazolo[1,5-a]-pyridin-2-yl)amino]ethyl}trimethylammonium salt

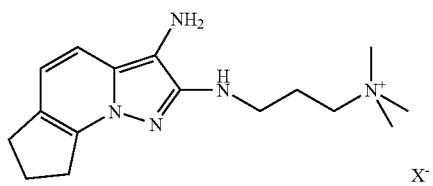

{3-[(3-Amino-7,8-dihydro-6H-cyclopenta[e]pyrazolo[1,5-a]-pyridin-2-yl)amino]propyl}trimethylammonium salt

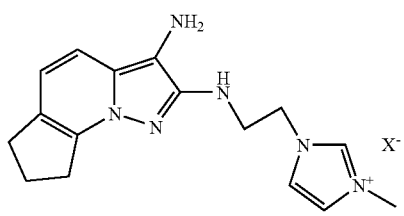

1-{2-[(3-Amino-7,8-dihydro-6H-cyclopenta[e]pyrazolo[1,5-a]-pyridin-2-yl)amino]ethyl}-3-methyl-1H-imidazol-3-ium salt

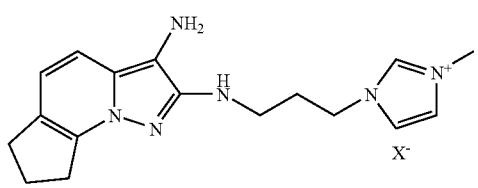

1-{3-[(3-Amino-7,8-dihydro-6H-cyclopenta[e]pyrazolo[1,5-a]-pyridin-2-yl)amino]propyl}-3-methyl-1H-imidazol-3-ium salt -continued

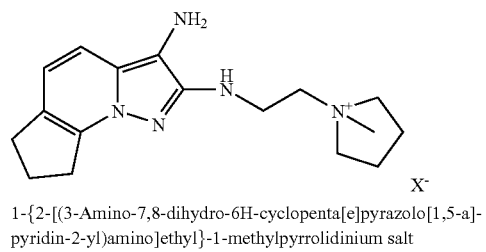

1-{2-[(3-Amino-7,8-dihydro-6H-cyclopenta[e]pyrazolo[1,5-a]-pyridin-2-yl)amino]ethyl}-1-methylpyrrolidinium salt

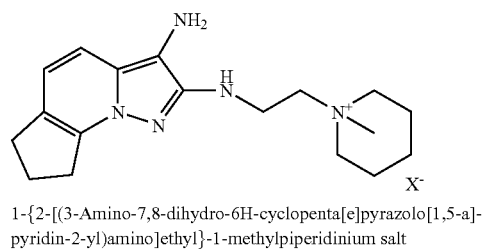

1-{2-[(3-Amino-7,8-dihydro-6H-cyclopenta[e]pyrazolo[1,5-a]-pyridin-2-yl)amino]ethyl}-1-methylpiperidinium salt

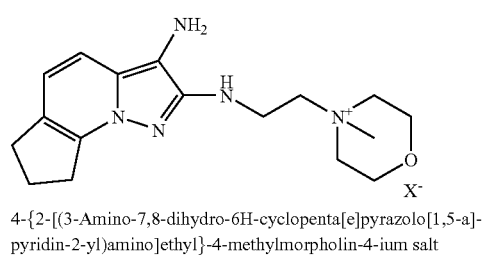

4-{2-[(3-Amino-7,8-dihydro-6H-cyclopenta[e]pyrazolo[1,5-a]-pyridin-2-yl)amino]ethyl}-4-methylmorpholin-4-ium salt

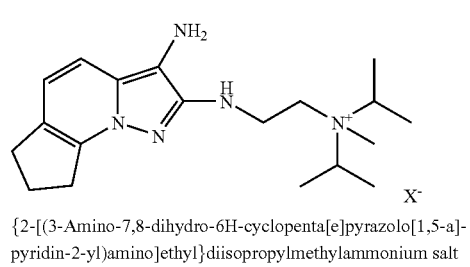

{2-[(3-Amino-7,8-dihydro-6H-cyclopenta[e]pyrazolo[1,5-a]-pyridin-2-yl)amino]ethyl}diisopropylmethylammonium salt

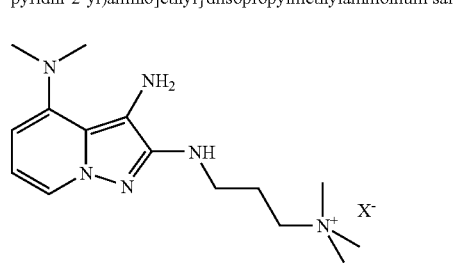

[3-(3-Amino-4-(dimethylamino)pyrazolo[1,5-a]pyridin-2-ylamino)propyl]trimethylammonium salt

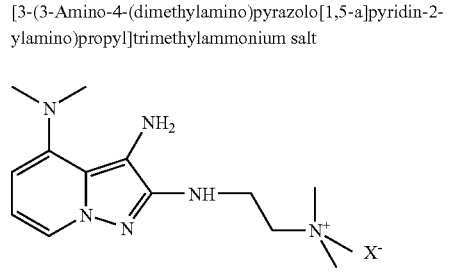

[2-(3-Amino-4-(dimethylamino)pyrazolo[1,5-a]pyridin-2-ylamino)ethyl]trimethylammonium salt

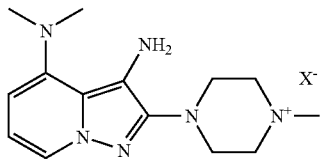

4-(3-Amino-4-(dimethylamino)pyrazolo[1,5-a]pyridin-2-yl)-1-methylpiperazin-1-ium salt

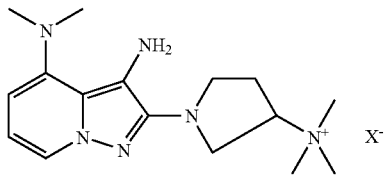

[1-(3-Amino-4-(dimethylamino)pyrazolo[1,5-a]pyridin-2-yl)-pyrrolidin-3-yl]trimethylammonium salt

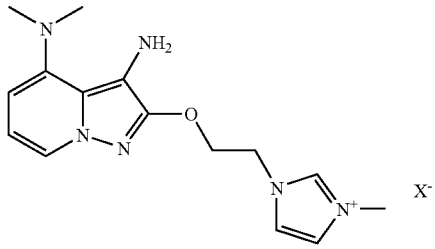

3-[2-(3-Amino-4-(dimethylamino)pyrazolo[1,5-a]pyridin-2-yloxy)ethyl]-1-methyl-3H-imidazol-1-ium salt

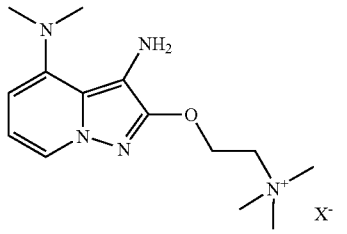

[2-(3-Amino-4-(dimethylamino)pyrazolo[1,5-a]pyridin-2-yloxy)ethyl]trimethylammonium salt

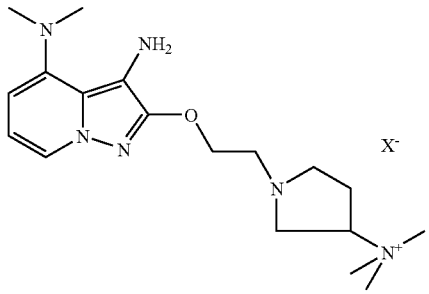

{1-[2-(3-Amino-4-(dimethylamino)pyrazolo[1,5-a]pyridin-2-yloxy)ethyl]pyrrolidin-3-yl}trimethylammonium salt

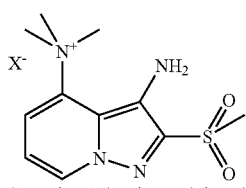

(3-Amino-2-(methanesulphonyl)pyrazolo[1,5-a]pyridin-4-yl)-trimethylammonium salt and

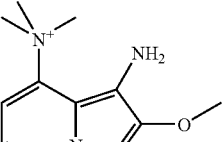

(3-Amino-2-methoxypyrazolo[1,5-a]pyridin-4-yl)tri-methylammonium salt.

9. The composition according to claim 1, wherein the at least one compound of formula (I) is present is an amount ranging from 0.001% to 10% by weight relative to the total weight of the dyeing composition.

10. The composition according to claim 1, wherein the at least one coupler is chosen from meta-phenylenediamines, meta-aminophenols, meta-diphenols, naphthalene couplers, heterocyclic couplers and their addition salts.

11. The composition according to claim 1, wherein the at least one $C_4$-$C_{30}$ polyol is chosen from $C_4$-$C_{15}$ polyols.

12. The composition according to claim 11, wherein the at least one $C_4$-$C_{15}$ polyol is chosen from hexylene glycol, neopentyl glycol, and isoprene glycol.

13. The composition according to claim 1, wherein the at least one $C_4$-$C_{30}$ polyol is present in an amount ranging from 0.1% to 40% by weight relative to the total weight of the dyeing composition.

14. A method for dyeing keratinous fibers, comprising applying to the keratinous fibers, in the presence of at least one oxidizing agent, for a time sufficient to develop the desired coloring, a composition comprising:

at least one aminopyrazolopyridine oxidation base chosen from those of formula (I):

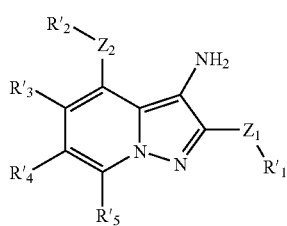

(I)

wherein:
$Z_1$ and $Z_2$ are each independently chosen from:
a simple covalent bond,
divalent radicals chosen from:
—O(CH$_2$)$_p$— radicals, wherein p is an integer ranging from 0 to 6,
—NR'$_6$(CH$_2$)$_q$(C$_6$H$_4$)$_t$— radicals, wherein q is an integer ranging from 0 to 6, t is 0 or 1, and R'$_6$ is chosen from a hydrogen atom and $C_1$-$C_6$ alkyl radicals optionally substituted by at least one hydroxyl group, and
when R'$_1$ is a methyl radical, $Z_1$ can also be chosen from divalent radicals —S—, —SO— and —SO$_2$—;
R'$_1$ and R'$_2$ are each independently chosen from:
a hydrogen atom,
optionally substituted $C_1$-$C_{10}$ alkyl radicals, optionally interrupted by a heteroatom or a group chosen from O, N, Si, S, SO and SO$_2$,
halogen atoms, SO₃H radicals,
saturated, unsaturated, aromatic, substituted and unsubstituted 5- to 8-membered ring optionally comprising at least one heteroatom or group chosen from N, O, S, SO₂ and —CO—, it being possible for the ring to be cationic and/or substituted by a cationic radical,
—N⁺R₁₇R₁₈R₁₉ groups, wherein R₁₇, R₁₈ and R₁₉ are chosen from linear and branched C₁-C₅ alkyl radicals which are optionally substituted by at least one hydroxyl group, and
when Z₁, is a covalent bond, then R'₁ can also be chosen from:
optionally substituted C₁-C₆ alkylcarbonyl radicals, and —O—CO—R, —CO—O—R, NR—CO—R' and —CO—NRR' radicals wherein R and R' are independently chosen from a hydrogen atom and optionally substituted C₁-C₆ alkyl radicals, and
when Z₂ is a covalent bond, then R'₂ can also be chosen from:
optionally substituted C₁-C₆ alkylcarbonyl radicals, and —O—CO—R, —CO—O—R, NR—CO—R' and —CO—NRR' radicals wherein R and R' are independently chosen from a hydrogen atom and optionally substituted C₁-C₆ alkyl radicals;
R'₃, R'₄ and R'₅ are each independently chosen from:
a hydrogen atom,
hydroxyl radicals,
C₁-C₆ alkoxy radicals,
C₁-C₆ alkylthio radicals,
amino radicals,
monoalkylamino radicals,
C₁-C₆ dialkylamino radicals wherein the alkyl radicals can form, with the nitrogen atom to which they are attached, a saturated or unsaturated, aromatic or non-aromatic 5- to 8-membered heterocycle which may comprise at least one heteroatom or group chosen from N, O, S, SO₂ and CO, it being possible for the heterocycle to be cationic and/or substituted by a cationic radical,
optionally substituted C₁-C₆ alkylcarbonyl radicals,
—O—CO—R, —CO—O—R, NR—CO—R' and —CO—NRR' radicals with R and R' as defined above,
halogen atoms,
—NHSO₃H radicals,
optionally substituted C₁-C₄ alkyl radicals, and
saturated, unsaturated, aromatic and optionally substituted carbon rings,
it being possible for R'₃, R'₄ to R'₅ to form, in pairs, a ring which is optionally saturated; and
X— is chosen from electronegative ions or groups of ions;
wherein it is understood that at least one of the groups R'₁ and R'₂ is chosen from cationic radicals;
at least one coupler; and
at least one C₄-C₃₀ polyol comprising a saturated or unsaturated, linear, branched or cyclic hydrocarbon chain which carries at least two hydroxyl functions, the chain and its branches optionally substituted by at least one other substituent chosen from carboxyl, amino, halogens, C₆-C₃₀ aryl groups, polyethylene glycols comprising 4, 6 or 7 ethylene units, and dipropylene glycol.

15. The method according to claim 14, wherein the at least one oxidizing agent is chosen from hydrogen peroxide, urea hydrogen peroxide, alkali metal bromates, persalts, peracids and oxidase enzymes.

16. A multicompartment device comprising, in at least one first compartment, at least one dyeing composition comprising:
at least one aminopyrazolopyridine oxidation base chosen from those of formula (I):

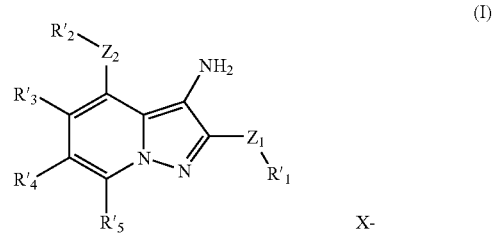

wherein:
Z₁ and Z₂ are each independently chosen from:
a simple covalent bond,
divalent radicals chosen from:
—O(CH₂)ₚ— radicals, wherein p is an integer ranging from 0 to 6, and
—NR'₆(CH₂)_q(C₆H₄)_t— radicals, wherein q is an integer ranging from 0 to 6, t is 0 or 1, and R'₆ is chosen from a hydrogen atom and C₁-C₆ alkyl radicals optionally substituted by at least one hydroxyl group, and
when R'₁ is a methyl radical, Z₁ can also be chosen from divalent radicals —S—, —SO— and —SO₂—;
R'₁ and R'₂ are each independently chosen from:
a hydrogen atom,
optionally substituted C₁-C₁₀ alkyl radicals, optionally interrupted by a heteroatom or a group chosen from O, N, Si, S, SO and SO₂,
halogen atoms,
SO₃H radicals,
saturated, unsaturated, aromatic, substituted and unsubstituted 5- to 8-membered ring optionally comprising at least one heteroatom or group chosen from N, O, S, SO₂ and —CO—, it being possible for the ring to be cationic and/or substituted by a cationic radical,
—N⁺R₁₇R₁₈R₁₉ groups, wherein R₁₇, R₁₈ and R₁₉ are chosen from linear and branched C₁-C₅ alkyl radicals which are optionally substituted by at least one hydroxyl group, and
when Z₁ is a covalent bond, then R'₁ can also be chosen from:
optionally substituted C₁-C₆ alkylcarbonyl radicals, and —O—CO—R, —CO—O—R, NR—CO—R' and —CO—NRR' radicals wherein R and R' are independently chosen from a hydrogen atom and optionally substituted C₁-C₆ alkyl radicals, and
when Z₂ is a covalent bonds, then R'₂, can also be chosen from:
optionally substituted C₁-C₆ alkylcarbonyl radicals, and —O—CO—R, —CO—O—R, NR—CO—R' and —CO—NRR' radicals wherein R and R' are independently chosen from a hydrogen atom and optionally substituted C₁-C₆ alkyl radicals;
R'₃, R'₄ and R'₅, which are identical or different, are chosen from:
a hydrogen atom,
hydroxyl radicals,
C₁-C₆ alkoxy radicals,
C₁-C₆ alkylthio radicals, amino radicals, monoalkylamino radicals, $C_1$-$C_6$ dialkylamino radicals wherein the alkyl radicals can form, with the nitrogen atom to which they are attached, a saturated or unsaturated, aromatic or non-aromatic 5- to 8-membered heterocycle which may comprise at least one heteroatom or group chosen from N, O, S, $SO_2$ and CO, it being possible for the heterocycle to be cationic and/or substituted by a cationic radical, optionally substituted $C_1$-$C_6$ alkylcarbonyl radicals, —O—CO—R, —CO—O—R, NR—CO—R' and —CO—NRR' radicals wherein R and R' as defined above, halogen atoms, —NHSO$_3$H radicals, optionally substituted $C_1$-$C_4$ alkyl radicals, and saturated, unsaturated, aromatic and optionally substituted carbon rings, it being possible for R'$_3$, R'$_4$ to R'$_5$ to form, in pairs, a ring which is optionally partially saturated;

X— is chosen from electronegative ions or groups of ions; wherein it is understood that at least one of the groups R'$_1$ and R'$_2$ is chosen from cationic radicals;

at least one coupler; and at least one $C_4$-$C_{30}$ polyol comprising a saturated or unsaturated, linear, branched or cyclic hydrocarbon chain comprising at least two hydroxyl functions, wherein the chain and its branches are optionally substituted by at least one other substituent chosen from carboxyl, amino, halogens, $C_6$-$C_{30}$ aryl groups, polyethylene glycols comprising 4, 6 or 7 ethylene units and dipropylene glycol, and in at least one second compartment, at least one oxidizing agent.

* * * * *

UNITED STATES PATENT AND TRADEMARK OFFICE
CERTIFICATE OF CORRECTION

| | |
|---|---|
| PATENT NO. | : 7,578,856 B2 |
| APPLICATION NO. | : 12/149872 |
| DATED | : August 25, 2009 |
| INVENTOR(S) | : Jean-Baptiste Saunier |

It is certified that error appears in the above-identified patent and that said Letters Patent is hereby corrected as shown below:

On the Title Page, insert the following missing data:

--(30)  Foreign Application Priority Data
May 9, 2007 (FR)         0754947--.

Signed and Sealed this

Twenty-seventh Day of October, 2009

David J. Kappos
*Director of the United States Patent and Trademark Office*